US011458211B2

(12) United States Patent
Pchejetsky et al.

(10) Patent No.: US 11,458,211 B2
(45) Date of Patent: Oct. 4, 2022

(54) GENE THERAPY

(71) Applicants: The University of Manchester, Manchester (GB); Centre Hospitalier Universitaire Sainte-Justine, Québec (CA); Alexey Pchejetsky, Mont-Royal (CA)

(72) Inventors: Alexey Pchejetsky, Mont-Royal (CA); Brian Bigger, Manchester (GB); Claire O'Leary, Manchester (GB)

(73) Assignees: The University of Manchester, Manchester (GB); Centre Hospitalier Universitaire Sainte-Justine, Québec (CA)

( * ) Notice: Subject to any disclaimer, the term of this patent is extended or adjusted under 35 U.S.C. 154(b) by 581 days.

(21) Appl. No.: 16/317,126

(22) PCT Filed: Jul. 12, 2017

(86) PCT No.: PCT/GB2017/052044
§ 371 (c)(1),
(2) Date: Jan. 11, 2019

(87) PCT Pub. No.: WO2018/011572
PCT Pub. Date: Jan. 18, 2018

(65) Prior Publication Data
US 2019/0314522 A1    Oct. 17, 2019

(30) Foreign Application Priority Data

Jul. 12, 2016  (GB) ..................... 1612104
Mar. 23, 2017  (GB) ..................... 1704634

(51) Int. Cl.
| C12N 15/79 | (2006.01) |
| C07H 21/04 | (2006.01) |
| A61K 48/00 | (2006.01) |
| A61K 9/00 | (2006.01) |
| A61K 38/45 | (2006.01) |
| A61K 45/06 | (2006.01) |
| C12N 9/10 | (2006.01) |
| C12N 15/86 | (2006.01) |

(52) U.S. Cl.
CPC .......... *A61K 48/005* (2013.01); *A61K 9/0085* (2013.01); *A61K 38/45* (2013.01); *A61K 45/06* (2013.01); *A61K 48/0075* (2013.01); *C12N 9/1029* (2013.01); *C12N 15/86* (2013.01); *C12Y 203/01078* (2013.01); *C12N 2750/14143* (2013.01); *C12N 2800/22* (2013.01)

(58) Field of Classification Search
CPC ........ C12N 15/79; C12N 15/85; C12N 15/86; C12N 2800/22; C07H 21/04
See application file for complete search history.

(56) References Cited

U.S. PATENT DOCUMENTS

2016/0060656 A1    3/2016  Rebar

FOREIGN PATENT DOCUMENTS

| EP | 2394667 A1 | 12/2011 |
| WO | WO 03/092594 A2 | 11/2003 |
| WO | WO 2013/164793 A2 | 11/2013 |
| WO | WO 2015/012924 A2 | 1/2015 |
| WO | WO 2015/121501 A1 | 8/2015 |
| WO | WO 2015/168666 A2 | 11/2015 |
| WO | WO 2015/173308 A1 | 11/2015 |

OTHER PUBLICATIONS

Fan et al., 2006, The American Journal of Human Genetics, vol. 79, p. 738-744.*
Chen et al., 2005, GenEmbl Accession No. AY695370, computer printout, p. 1-5.*
Nagata et al., "Codon Optimization Effect on Translational Efficiency of DNA Vaccine in Mammalian Cells: Analysis of Plasmid DNA Encoding a CTL Epitope Derived from Microorganisms," Biochemical and Biophysical Research Communications, vol. 261, No. 2, pp. 445-451 (Aug. 1999).
IPRP corresponding to International Patent Application No. PCT/GB2017/052044 dated Jan. 15, 2019.
Fraldi et al., "Functional correction of CNS lesions in an MPS-IIIA mouse model by intracerebral AAV-mediated delivery of sulfamidase and SUMF1 genes," Human Molecular Genetics, vol. 16, No. 22, pp. 2693-2702 (Nov. 2007).
Gilkes et al., "Mucopolysaccharidosis IIIB confers enhanced neonatal intracranial transduction by AAV8 but not by 5, 9 or rh10," Gene Therapy, vol. 23, No. 3, pp. 263-271(2016).
International Search Report and Written Opinion corresponding to International Patent Application No. PCT/GB2017/052044 dated Nov. 15, 2017.
Martins et al., "Neuroinflammation, mitochondrial defects and neurodegeneration in mucopolysaccharidosis III type C mouse model," Brain, vol. 138(Pt 2), pp. 336-355 (2015).
OMIM Entry—# 252930—Mucopolysaccharidosis, Type IIIC; MPS3C, dated Jun. 4, 1986 [retrieved Jan. 11, 2019].
Wilkinson et al., Neuropathology in Mouse Models of Mucopolysaccharidosis Type I, IIIA and IIIB, PLoS One, vol. 7, No. 4, e35787, pp. 1-18 (2012).

\* cited by examiner

*Primary Examiner* — Shin Lin Chen
(74) *Attorney, Agent, or Firm* — Jenkins, Wilson, Taylor & Hunt, P.A.

(57) ABSTRACT

The present invention relates to compositions and adeno associated viral vectors comprising an optimised HGSNAT nucleic acid sequence of SEQ ID No. 1 or a derivative sequence having at least 77% homology thereof. Uses of such compositions and vectors are also contemplated along with kits of parts for their administration.

Figure 1:
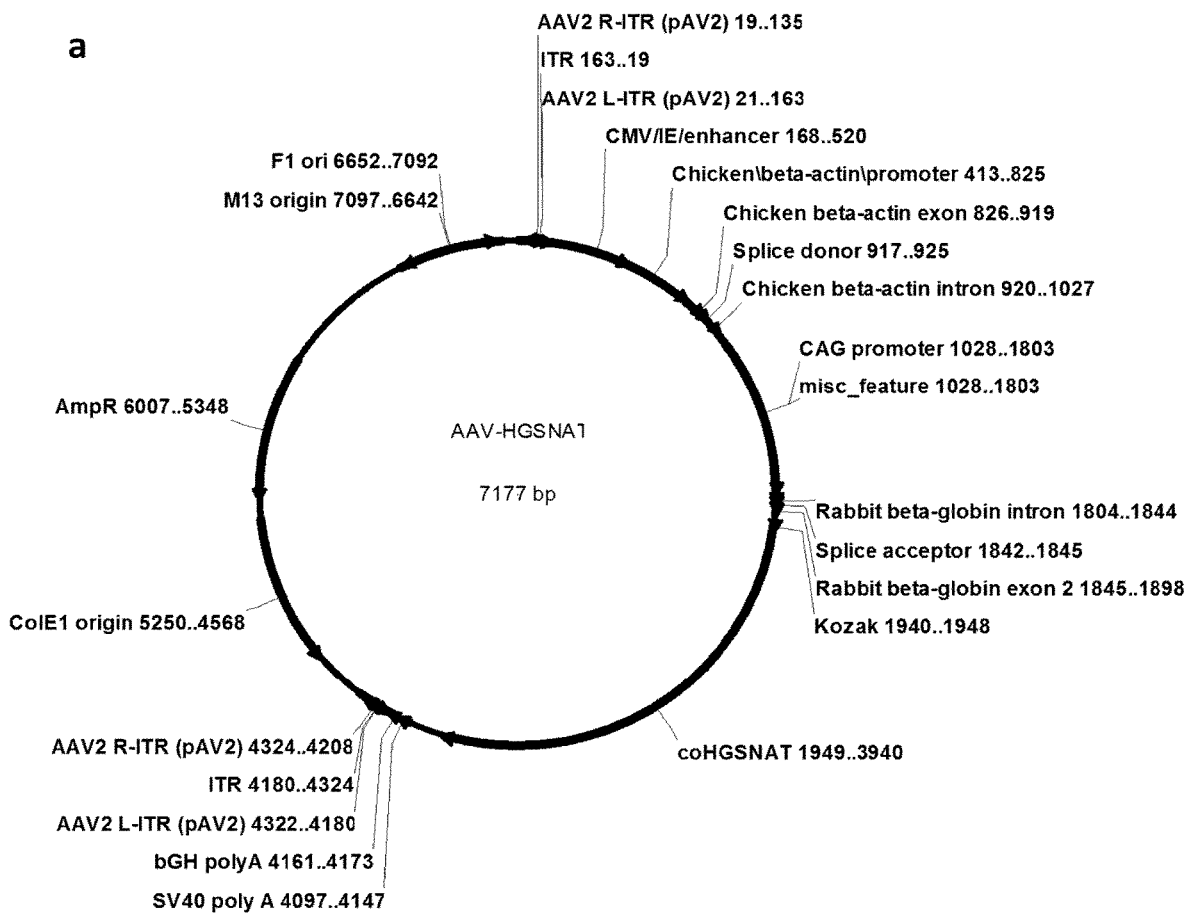
Figure 1:
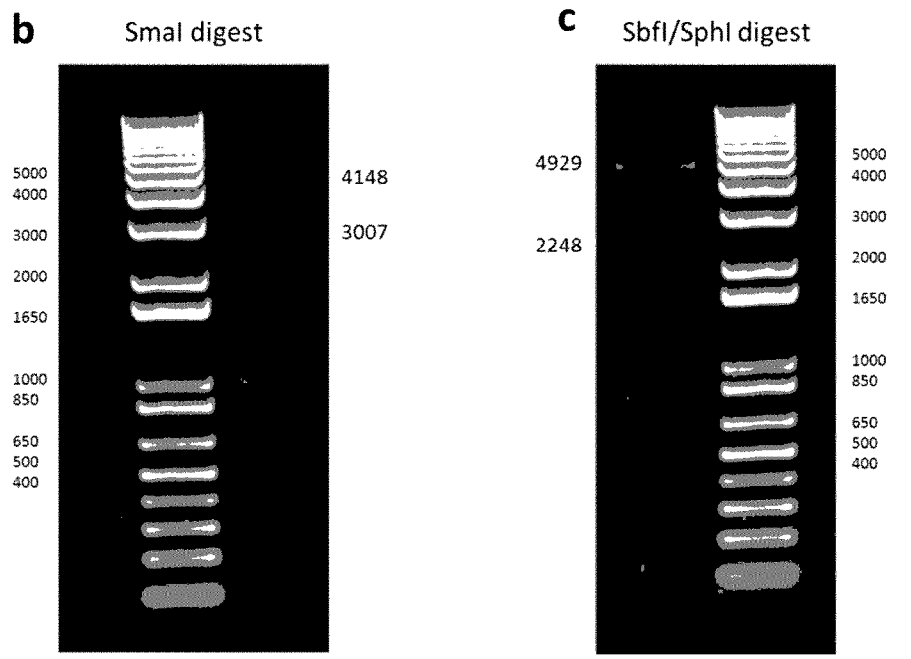

15 Claims, 27 Drawing Sheets
Specification includes a Sequence Listing.

a b d   AAV9 e   AAV-TT f   AAV-rh10 g h i j (1)

(2)

(3)

SEQUENCE LISTING

<160> NUMBER OF SEQ ID NOS: 6

<210> SEQ ID NO 1
<211> LENGTH: 7177
<212> TYPE: DNA
<213> ORGANISM: Artificial Sequence
<220> FEATURE:
<223> OTHER INFORMATION: Optimised HGSNAT sequence

<400> SEQUENCE: 1

```
gggggggggg ggggggggtt ggccactccc tctctgcgcg ctcgctcgct cactgaggcc     60
gggcgaccaa aggtcgcccg acgcccgggc tttgcccggg cggcctcagt gagcgagcga    120
gcgcgcagag agggagtggc caactccatc actaggggtt cctagatctg aattcggtac    180
cctagttatt aatagtaatc aattacgggg tcattagttc atagcccata tggagttc      240 cgcgttacat aacttacggt aaatggcccg cctggctgac cgcccaacga ccccgccca     300 ttgacgtcaa taatgacgta tgttcccata gtaacgccaa tagggacttt ccattgacgt    360
caatgggtgg actatttacg gtaaactgcc cacttggcag tacatcaagt gtatcatatg    420
ccaagtacgc ccctattga cgtcaatgac ggtaaatggc ccgcctggca ttatgcccag     480
tacatgacct tatgggactt tcctacttgg cagtacatct acgtattagt catcgctatt    540
accatggtcg aggtgagccc cacgttctgc ttcactctcc ccatctcccc ccctcccca    600
```

```
cccccaattt tgtatttatt tattttttaa ttattttgtg cagcgatggg ggcgggggggg      660 ggggggggc gcgcgccagg cggggcgggg cgggcgagg ggcggggcgg ggcgaggcgg          720
agaggtgcgg cggcagccaa tcagagcggc gcgctccgaa agtttcctt tatggcgagg         780 cggcggcggc ggcggcccta taaaaagcga agcgcgcggc gggcgggagt cgctgcgacg        840
ctgccttcgc cccgtgcccc gctccgccgc cgcctcgcgc cgcccgcccc ggctctgact        900
gaccgcgtta ctcccacagg tgagcgggcg ggacggccct tctcctccgg gctgtaatta       960
gcgcttggtt taatgacggc ttgtttcttt tctgtggctg cgtgaaagcc ttgaggggct       1020
ccgggagggc cctttgtgcg gggggagcg gctcggggg tgcgtgcgtg tgtgtgtgcg        1080
tggggagcgc cgcgtgcggc ccgcgctgcc cggcggctgt gagcgctgcg ggcgcggcgc      1140
ggggctttgt gcgctccgca gtgtgcgcga ggggagcgcg gccggggcg gtgccccgcg        1200 gtgcgggggg ggctgcgagg ggaacaaagg ctgcgtgcgg ggtgtgtgcg tgggggggtg      1260 agcaggggt gtgggcgcgg cggtcgggct gtaaccccc cctgcacccc cctccccgag        1320
ttgctgagca cggcccggct tcgggtgcgg ggctccgtac ggggcgtggc gcgggctcg       1380 ccgtgccggg cggggggtgg cggcaggtgg gggtgccggg cggggcgggg ccgcctcggg      1440
ccggggaggg ctcgggggag gggcgcggcg gcccccggag cgccggcggc tgtcgaggcg      1500
cggcgagccg cagccattgc cttttatggt aatcgtgcga gagggcgcag ggacttcctt     1560
tgtcccaaat ctgtgcggag ccgaaatctg ggaggcgccg ccgcaccccc tctagcgggc     1620
gcggggcgaa gcggtgcggc gccggcagga aggaaatggg cggggagggc cttcgtgcgt    1680
cgccgcgccg ccgtccccctt ctccctctcc agcctcgggg ctgtccgcgg ggggacggct   1740
gccttcgggg gggacgggggc agggcggggt tcggcttctg gcgtgtgacc ggcggctcta   1800
gagcctctgc taaccatgtt catgccttct tcttttttcct acagctcctg ggcaacgtgc   1860
tggttattgt gctgtctcat cattttggca aagaattcct cgaagatcta ggcctgcagg    1920
accggactca gatctcgagg ccgccaccat gactggagca agagcatcag cagcagagca     1980
gagaagagca gggagatcag gacaggcacg ggcagcagaa agagcagcag gaatgagcgg      2040
agcaggaagg gcactggcag ctctgctgct ggcagccagt gtgctgtcag ctgcactgct      2100
ggcacctgga ggaagctccg gacgagacgc acaggcagct ccccctagag acctggataa    2160
gaaaaggcac gccgaactga agatggatca ggctctgctg ctgatccata cgagctgct      2220 gtggacaaat ctgactgtgt actggaaaag cgaatgctgt tatcactgcc tgttccaggt     2280
gctggtcaac gtgccacagt ctcccaaggc cgggaaacca agtgcagccg ctgcatctgt     2340
gagtacccag catggaagca tcctgcagct gaacgacaca ctggaggaaa aggaggtgtg     2400
caggctggaa taccgcttcg gagagtttgg caattatagc ctgctggtca aaaacattca     2460
caatggggtg tccgaaatcg cttgtgatct ggcagtcaac gaggacccag tggatagcaa    2520
tctgcccgtg tccattgcct ttctgatcgg cctggctgtc atcattgtga tttcattcct    2580
gcggctgctg ctgagcctgg acgattttaa caattggatt agcaaggcta tctctagtcg    2640
agaaacagac cggctgatca atagcgagct gggctcaccc agccggactg atcctctgga    2700
cggggatgtg cagccagcaa cctggagact gagtgcactg ccaccacgac tgagatcagt    2760
ggacactttc agaggcattg ccctgatcct gatggtcttt gtgaactacg gaggcgggaa    2820
gtactggtat ttcaaacatg cttcctggaa tggactgacc gtcgcagatc tggtgttccc    2880
ctggttcgtg tttattatgg gctcaagcat ctttctgagc atgacatcca ttctgcagcg    2940
```

```
cggctgttct aagttccgac tgctggggaa aatcgcctgg aggagttttc tgctgatttg   3000
catcggaatc attatcgtga accctaatta ttgtctgggc ccactgtctt gggacaaagt   3060
caggatccca ggagtgctgc agcgactggg agtcacttac ttcgtggtcg cagtgctgga   3120
gctgctgttt gccaaacctg tgccagaaca ctgcgcctct gagcggagtt gtctgtcact   3180
gagagatatt acctcctctt ggccccagtg gctgctgatc ctggtgctgg aggggctgtg   3240
gctgggactg acattcctgc tgccagtgcc tggatgccca actgggtatc tgggacctgg   3300
aggcattggc gactttggga agtatcctaa ctgtaccggg ggagccgctg gatacatcga   3360
tcgcctgctg ctgggcgacg atcacctgta ccagcatcca agttcagccg tcctgtacca   3420
tacagaagtg gcttatgacc ccgagggaat tctgggcact attaatagca tcgtcatggc   3480
tttcctgggc gtgcaggcag ggaagatcct gctgtactat aaggctcgaa ctaaagatat   3540
tctgatccgc tttaccgcat ggtgctgtat tctgggcctg atctccgtcg ccctgacaaa   3600
ggtgtctgag aacgaagggt tcattcctgt caacaaaaat ctgtggtccc tgtcttatgt   3660
gaccacactg agctcctttg ccttctttat cctgctggtc ctgtacccag tggtcgacgt   3720
gaagggactg tggactggca cccctttctt tacccaggg atgaactcca tcctggtcta   3780
tgtgggacac gaggtgttcg aaaattactt cccttttcag tggaagctga agataacca   3840 gtctcacaaa gagcatctga cccagaatat cgtggccaca gccctgtggg tcctgattgc   3900
ctatatcctg tatcggaaga gattttctg gaagatttga gggcgcggcc gcgactctag   3960
atcataatca gccataccac atttgtagag gttttacttg ctttaaaaaa cctcccacac   4020
ctccccctga acctgaaaca taaaatgaat gcaattgttg ttgttaactt gtttattgca   4080
gcttataatg gttacaaata aagcaatagc atcacaaatt tcacaaataa agcatttttt   4140
tcactgcatt ctagttgtgg gcatgctggg gagagatcta ggaaccccta gtgatggagt   4200
tggccactcc ctctctgcgc gctcgctcgc tcactgaggc cgcccgggca agcccgggc   4260 gtcgggcgac ctttggtcgc ccggcctcag tgagcgagcg agcgcgcaga gagggagtgg   4320 ccaaccccc ccccccccc cctgcagccc tgcattaatg aatcggccaa cgcgcgggga   4380
gaggcggttt gcgtattggg cgctcttccg cttcctcgct cactgactcg ctgcgctcgg   4440
tcgttcggct gcggcgagcg gtatcagctc actcaaaggc ggtaatacgg ttatccacag   4500
aatcagggga taacgcagga aagaacatgt gagcaaaagg ccagcaaaag gccaggaacc   4560
gtaaaaaggc cgcgttgctg gcgtttttcc ataggctccg cccccctgac gagcatcaca   4620
aaaatcgacg ctcaagtcag aggtggcgaa acccgacagg actataaaga taccaggcgt   4680
ttccccctgg aagctccctc gtgcgctctc ctgttccgac cctgccgctt accggatacc   4740
tgtccgcctt tctcccttcg ggaagcgtgg cgctttctca atgctcacgc tgtaggtatc   4800
tcagttcggt gtaggtcgtt cgctccaagc tgggctgtgt gcacgaaccc cccgttcagc   4860
ccgaccgctg cgccttatcc ggtaactatc gtcttgagtc aacccggta agacacgact   4920 tatcgccact ggcagcagcc actggtaaca ggattagcag agcgaggtat gtaggcggtg   4980
ctacagagtt cttgaagtgg tggcctaact acggctacac tagaaggaca gtatttggta   5040
tctgcgctct gctgaagcca gttaccttcg gaaaaagagt tggtagctct tgatccggca   5100
aacaaaccac cgctggtagc ggtggttttt tgtttgcaa gcagcagatt acgcgcagaa   5160
aaaaaggatc tcaagaagat cctttgatct tttctacggg gtctgacgct cagtggaacg   5220
aaaactcacg ttagggatt ttggtcatga gattatcaaa aaggatcttc acctagatcc   5280
ttttaaatta aaaatgaagt tttaaatcaa tctaaagtat atatgagtaa acttggtctg   5340
```

```
acagttacca atgcttaatc agtgaggcac ctatctcagc gatctgtcta tttcgttcat    5400
ccatagttgc ctgactcccc gtcgtgtaga taactacgat acgggagggc ttaccatctg    5460
gccccagtgc tgcaatgata ccgcgagacc cacgctcacc ggctccagat ttatcagcaa    5520
taaaccagcc agccggaagg gccgagcgca gaagtggtcc tgcaacttta tccgcctcca    5580
tccagtctat taattgttgc cgggaagcta gagtaagtag ttcgccagtt aatagtttgc    5640
gcaacgttgt tgccattgct acaggcatcg tggtgtcacg ctcgtcgttt ggtatggctt    5700
cattcagctc cggttcccaa cgatcaaggc gagttacatg atccccatg ttgtgcaaaa    5760 aagcggttag ctccttcggt cctccgatcg ttgtcagaag taagttggcc gcagtgttat    5820
cactcatggt tatggcagca ctgcataatt ctcttactgt catgccatcc gtaagatgct    5880
tttctgtgac tggtgagtac tcaaccaagt cattctgaga atagtgtatg cggcgaccga    5940
gttgctcttg cccggcgtca atacgggata taccgcgcc acatagcaga actttaaaag    6000
tgctcatcat tggaaaacgt tcttcggggc gaaaactctc aaggatctta ccgctgttga    6060
gatccagttc gatgtaaccc actcgtgcac ccaactgatc ttcagcatct tttactttca    6120
ccagcgtttc tgggtgagca aaaacaggaa ggcaaaatgc cgcaaaaaag gaataagggc    6180 gacacggaa atgttgaata ctcatactct tcctttttca atattattga agcatttatc    6240
agggttattg tctcatgagc ggatacatat ttgaatgtat ttagaaaaat aaacaaatag    6300
gggttccgcg cacatttccc cgaaaagtgc cacctgacgt ctaagaaacc attattatca    6360
tgacattaac ctataaaaat aggcgtatca cgaggccctt tcgtctcgcg cgtttcggtg    6420
atgacggtga aaacctctga cacatgcagc tcccggagac ggtcacagct tgtctgtaag    6480
cggatgccgg gagcagacaa gcccgtcagg gcgcgtcagc gggtgttggc gggtgtcggg    6540
gctggcttaa ctatgcggca tcagagcaga ttgtactgag agtgcaccat atgcggtgtg    6600
aaataccgca cagatgcgta aggagaaaat accgcatcag gaaattgtaa acgttaatat    6660
tttgttaaaa ttcgcgttaa attttttgtta aatcagctca ttttttaacc aataggccga    6720
aatcggcaaa atcccttata aatcaaaaga atagaccgag ataggggttga gtgttgttcc    6780 agtttggaac aagagtccac tattaaagaa cgtggactcc aacgtcaaag ggcgaaaaac    6840
cgtctatcag ggcgatggcc cactacgtga accatcaccc taatcaagtt ttttggggtc    6900
gaggtgccgt aaagcactaa atcggaaccc taaaggagc ccccgattta gagcttgacg    6960
gggaaagccg cgaacgtgg cgagaaagga agggaagaaa gcgaaaggag cgggcgctag    7020
ggcgctggca agtgtagcgg tcacgctgcg cgtaaccacc acaccccgccg cgcttaatgc    7080 gccgctacag ggcgcgtcgc gccattcgcc attcaggcta cgcaactgtt gggaagggcg    7140
atcggtgcgg gcctcttcgc tattacgcca ggctgca                             7177
```

<210> SEQ ID NO 2
<211> LENGTH: 735
<212> TYPE: PRT
<213> ORGANISM: Artificial Sequence
<220> FEATURE:
<223> OTHER INFORMATION: Synthetic sequence: Amino acid sequence of
      true-type adeno-associated virus 2 (ttAAV2) capsid protein

<400> SEQUENCE: 2

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30
```

```
Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Ile Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Ala Glu Pro Asp Ser Ser Gly Thr Gly
145                 150                 155                 160

Lys Ser Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Ser Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445
```

-continued

```
Asn Thr Pro Ser Gly Thr Thr Thr Met Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ala Ala Asp Asn Asn
                485                 490                 495
Asn Ser Asp Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Tyr Phe Pro Gln Ser Gly Val Leu Ile Phe Gly Lys
530                 535                 540
Gln Asp Ser Gly Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Ser Gly Asn Thr Gln Ala Ala Thr
                580                 585                 590
Ser Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 3
<211> LENGTH: 735
<212> TYPE: PRT
<213> ORGANISM: adeno-associated virus 2

<400> SEQUENCE: 3

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
                35                  40                  45
Gly Tyr Lys Tyr Leu Gly Pro Phe Asn Gly Leu Asp Lys Gly Glu Pro
            50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
```

```
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Pro Val Lys Thr Ala Pro Gly Lys Lys Arg
130             135                 140

Pro Val Glu His Ser Pro Val Glu Pro Asp Ser Ser Gly Thr Gly
145             150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510
```

```
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
        530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: adeno-associated virus 9

<400> SEQUENCE: 4

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
```

-continued

```
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
```

```
Tyr Gly Gln Val Ala Thr Asn His Gln Ser Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 738
<212> TYPE: PRT
<213> ORGANISM: adeno-associated virus 10

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220
```

-continued

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
        500                 505                 510

Leu Asn Gly Arg Asp Ser Leu Val Asn Pro Gly Val Ala Met Ala Thr
    515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
            565                 570                 575

Glu Gln Tyr Gly Val Val Ala Asp Asn Leu Gln Gln Asn Ala Ala
        580                 585                 590

Pro Ile Val Gly Ala Val Asn Ser Gln Gly Ala Leu Pro Gly Met Val
    595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640
```

```
Gly Leu Lys His Pro Pro Gln Ile Leu Ile Lys Asn Thr Pro Val
            645                 650                 655
Pro Ala Asp Pro Pro Thr Thr Phe Ser Gln Ala Lys Leu Ala Ser Phe
        660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
        690                 695                 700
Ser Asn Tyr Tyr Lys Ser Thr Asn Val Asp Phe Ala Val Asn Thr Asp
705                 710                 715                 720
Gly Thr Tyr Ser Glu Pro Arg Pro Ile Gly Thr Arg Tyr Leu Thr Arg
                725                 730                 735
Asn Leu
```

<210> SEQ ID NO 6
<211> LENGTH: 738
<212> TYPE: PRT
<213> ORGANISM: adeno-associated virus 8

<400> SEQUENCE: 6

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ala Thr Asn Asp
            260                 265                 270
```

```
Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
```

-continued

```
            690                 695                 700
Ser Asn Tyr Tyr Lys Ser Thr Ser Val Asp Phe Ala Val Asn Thr Glu
705                     710                 715                 720

Gly Val Tyr Ser Glu Pro Arg Pro Ile Gly Thr Arg Tyr Leu Thr Arg
                    725                 730                 735

Asn Leu
```

GENE THERAPY

TECHNICAL FIELD OF THE INVENTION

The present invention relates to intracranial gene therapies mediated by specific adeno associated viral vectors. The present invention is particularly suited to the treatment of mucopolysaccharidosis (MPS) IIIC using an optimised HGSNAT gene sequence.

BACKGROUND TO THE INVENTION

Mucopolysaccharidosis (MPS) IIIC (OMIM #252930) is caused by mutations in the HGSNAT gene encoding heparin-α-glucosaminide N-acetyltransferase (EC 2.3.1.78), and has a prevalence of 0.21 per 100,000 live births, with cellular accumulation of the GAG heparan sulphate (HS) and severe clinical manifestations in the brain. It is clinically indistinguishable from MPSIIIA and MPSIIIB; both of which are caused by defects in other lysosomal enzymes which also catabolise HS. HGSNAT is also known as TMEM76 and the protein (EC 2.3.1.78) is also known as acetyl-CoA:heparan-α-D-glucosaminide N-acetyltransferase. The resulting deficiency in the lysosomal enzyme heparin-α-glucosaminide N-acetyltransferase, results in a progressive accumulation of undegraded HS in all cells of the body. Despite systemic HS accumulation, the main symptoms are in the brain with only mild somatic features. Either as a result of primary storage material, or as a consequence of inefficient functioning of lysosomal pathways including autophagy, proteasome dysfunction, synaptic vesicle function, there is secondary storage of other molecules in the brain including GM2 and GM3 gangliosides, cholesterol, accompanied by massive neuroinflammation and ultimately neuronal loss. Subsequent to these factors, progressive cognitive and later motor loss is observed in patients, severe behavioural disturbances and ultimately death by mid-thirties.

The primary cellular GAG storage is within the lysosomes of cells throughout the body, however, this is seen intracellularly and extracellularly as the disease progresses. Elevated HS has been shown to be in the plasma, urine and within tissues with increased lysosomal compartment size and vacuolation in cells. In the mouse model of MPSIIIC, storage of HS in the lysosomes has been shown to cause compromise in endocytic, lysosomal and autophagic functions, neuronal signalling is disrupted. Secondary storage of GM2, GM3 gangliosides and cholesterol is observed amongst other factors. In the brain signs of neuroinflammation including cytokine production enlarged and, activated microglia and astrocytosis is also observed. Patients follow a similar profile but also demonstrate subsequent neuronal loss.

Patients with MPS IIIC have a disorder marked by severe neurological symptoms. These include progressive dementia, challenging behaviour, hyperactivity, seizures and disrupted sleep. Unlike other MPS conditions, somatic features tend to be mild. The disorder tends to have three main stages. During the first stage, early mental and motor skill development may be somewhat delayed. Affected children show a marked decline in learning between ages 1 and 6, followed by eventual loss of language skills by age 25 and loss of some or all hearing. In the syndrome's second stage, aggressive behaviour, hyperactivity and irregular sleep may make children with MPSIIIC difficult to care for, particularly those who retain normal physical strength. In the syndrome's last stage, patients become increasingly unsteady and become unable to walk between ages 21-31. There is wide phenotypic variability.

The symptoms in patients with MPS IIIC may present as early as 1-2 years of age, but because of the mild somatic abnormalities, diagnosis is usually only established between the ages of 2 and 7 years. Untreated patients experience progressive neurologic deterioration and early death often complicated by epilepsy, neurological dysphagia and loss of all motor skills. Death usually occurs by age 35. There is no approved treatment for MPS IIIC.

The HGSNAT enzyme is a membrane bound lysosomal hydrolase, meaning that it does not follow the secretion/uptake pathways of other lysosomal hydrolases via either mannose-6-phosphate receptors or mannose receptors on the cell surface. Because of this, any treatment approaches relying on enzyme cross-correction, and receptor mediated endocytosis, will ultimately be unsuccessful in this disease. The main focus of treatment of other MPS diseases is to replace the deficient enzyme either by intravenous Enzyme Replacement Therapy (ERT) ERT or Haematopoietic Stem Cell Transplantation (HSCT).

Currently, therapies such as ERT are not an option for patients with MPS IIIC, as delivering intravenous enzyme will firstly be unable to cross-correct affected cells, due to the membrane bound nature of the enzyme and secondly have no effect on neurological functioning as lysosomal enzymes cannot cross the blood brain barrier.

Some companies have focussed on intrathecal enzyme delivery, or on fusion enzymes linked to blood brain barrier transporters, but due to the cross-correction problem in MPSIIIC, none of these approaches are suitable. HSCT cannot be used as the HGSNAT enzyme is a membrane bound protein, which cannot be delivered to deficient cells from donor hematopoietic cells via cross-correction, despite the ability to access the brain via monocyte derived microglial cells. Whilst ex vivo gene therapy approaches, developed by the inventors, for MPSIIIA and IIIB relying on overexpression of enzyme from a gene therapy vector integrated into the genome of transduced haematopoietic stem cells (HSC-gene therapy), proved very effective in diseases where cross-correction can occur, such approaches are inappropriate for MPSIIIC, due to the inability to cross-correct the disease.

One treatment approach that works in MPSIIIC is the substrate reduction therapy approach (SRT) or substrate optimisation therapy approach. This approach is based on either reducing the body's natural production of the primary substrate accumulated in MPSIIIC-HS, or in the case of substrate optimisation, reducing the production of the specific class of HS accumulated, as this is a complex carbohydrate. The inventors have shown that SRT is effective at delaying neurodegeneration in a mouse model of MPSIIIB using the drug genistein, which blocks proteoglycan production in cells, and have recently begun a phase III clinical trial to evaluate this treatment in patients with MPSIIIA, IIIB and IIIC as the mechanism is identical for all of these diseases. However, SRT or SOT will only delay disease onset, as completely blocking HS production is toxic to the cells. As there is no other degradation pathway for HS to follow, ultimately, even with SRT, the disease will still manifest eventually.

There have been other approaches based on either chaperone therapy to improve folding of misfolded HGSNAT protein (Amicus) or stop codon read-through that may work for MPSIIIC, but these will only ever target a subset of patients and depend on drugs that can cross the blood-brain barrier. Anti-inflammatories are also an area of research for MPS diseases, but nothing has entered clinical trial for Sanfilippo disease to date, and as these approaches do not target the underlying defect, their chance of success is relatively low.

In vivo direct gene therapy approaches are perhaps more suitable, assuming that they can be targeted to as many affected cells as possible and also have the potential to be used in combination with all of the above approaches to improve overall outcomes in patients. Most vector delivery is to the liver and spleen following intravenous AAV delivery and not to the brain.

Sadly, there are currently no approved treatments for MPSIIIC.

It is an object of the present invention to overcome one or more of the problems associated with the above proposed therapies for MPSIIIC. It is also an object of the present invention to provide an effective treatment for MPSIIIC. Such a treatment would ideally be relatively easy to administer and have a low toxicological profile. It would also be desirable if such a treatment was able to overcome or obviate issues concerned with administering treatments which need to cross the blood brain barrier.

SUMMARY OF THE INVENTION

In accordance with a first aspect of the present invention, there is provided a composition comprising an optimised HGSNAT nucleic acid sequence of SEQ ID No. 1 or a derivative sequence having at least 77% homology thereof.

The optimised HGSNAT nucleic acid sequence of SEQ ID No. 1 has 76% homology with the wild type sequence. The sequence may be any derivative sequence having at greater degree of homology to SEQ ID No. 1 than with the wild type sequence. The sequence may be a derivative sequence having at least 78% homology with SEQ ID No. 1. More preferred, the derivative sequence has at least 80%, at least 85% or at least 90% homology with SEQ ID No. 1. Even more preferred, the sequence may be a derivative sequence having at least 95%, at least 96%, at least 97%, at least 98% or at least 99% homology with SEQ ID No. 1.

The nucleic acid sequence may be a DNA, RNA, cDNA, or PNA and may be recombinant or synthetic. It may be single stranded or double stranded. The nucleic acid sequence will encode the optimised HGSNAT nucleic acid sequence of SEQ ID No. 1, or derivative sequence thereof. The nucleic acid sequence may be derived by cloning, for example using standard molecular cloning techniques including restriction digestion, ligation, gel electrophoresis (for example as described in Sambrook et al; Molecular Cloning: A laboratory manual, Cold Spring Harbour laboratory Press). The nucleic acid sequence may be isolated or amplified using PCR technology. Such technology may employ primers based upon the sequence of the nucleic acid sequence to be amplified. With the sequence information provided, the skilled person can use available cloning techniques to produce a nucleic acid sequence or vector suitable for transduction into a cell.

The optimised HGSNAT nucleic acid sequence may be optimised in a number of ways so as to enable enhanced expression or activity. For example the sequence may have been codon optimised by selecting codons most common in human cells and/or reducing one or more secondary structures and hairpins which may arise in subsequently formed mRNA and/or inserting a Kozak sequence at the ATG start site.

So as to further enhance expression or activity, the optimised HGSNAT nucleic acid sequence may be under the control of a suitable promoter. It is preferred that the promoter is a hybrid/fusion promoter, such as a CAG promoter (which is acytomegalovirus (CMV) enhancer fused to the chicken beta-actin promoter). Other promoters which may be utilised comprise: CMV; CBA; UBC; GUSB; NSE; Synapsin; MeCP2; and GFAP.

The optimised HGSNAT nucleic acid sequence may be flanked by inverted terminal repeats and may contain the cis acting elements from adeno associated virus 2 (AAV2).

Preferably, the optimised HGSNAT nucleic acid sequence, or derivative sequence thereof, is provided with, in or as part of an expression vector. Preferably, it may be provided as a gene therapy vector, preferably which is suitable for transduction and expression intracranially. The vector may be viral or non-viral (e.g. a plasmid). Viral vectors include those derived from adenovirus, adeno-associated virus (AAV) including mutated forms, retrovirus, lentivirus, herpes virus, vaccinia virus, MMLV, GaLV, Simian Immune Deficiency Virus (SIV), HIV, pox virus, and SV40. A viral vector is preferably replication defective, although it is envisaged that it may be replication deficient, replication competent or conditional. A viral vector may typically persist in an extrachromosomal state without integrating into the genome of the target neural cells. A preferred viral vector is an AAV vector. Selective targeting may be achieved using a specific AAV serotype (AAV serotype 2 to AAV serotype 12) or a modified version of any of these serotypes including true type variants.

The viral vector may be modified to delete any non-essential sequences. For wild type AAV, replication is unable to take place without the presence of helper virus, such as adenovirus. For recombinant adeno-associated virus, preferably the replication and capsid genes are provided in trans (in pRep/Cap plasmid), and only the 2 ITRs of AAV genome are left and packaged into a virion, while the adenovirus genes required are provided either provided by adenovirus or another plasmid. Similar functional modifications may be made to a lentiviral vector where appropriate.

The viral vector has the ability to enter a cell. However, a non-viral vector such as plasmid may be complexed with an agent to facilitate its uptake by a target cell. Such agents include polycationic agents. Alternatively, a delivery system such as a liposome based delivery system may be used.

The vector for use in the present invention is preferably suitable for use in vivo or in vitro, and is preferably suitable for use in a human.

The vector will preferably comprise one or more regulatory sequences to direct expression of the optimised HGSNAT nucleic acid sequence, or derivative sequence thereof. A regulatory sequence may include a promoter operably linked to the nucleic acid sequence, an enhancer, a transcription termination signal, a polyadenylyation sequence, an origin of replication, a nucleic acid restriction site, and a homologous recombination site. A vector may also include a selectable marker, for example to determine expression of the vector in a growth system (for example a bacterial cell) or in a target neural cell.

By "operably linked" means that the nucleic acid sequence is functionally associated with the sequence to which it is operably linked, such that they are linked in a manner such that they affect the expression or function of one another. For example, a nucleic acid sequence operably linked to a promoter will have an expression pattern influenced by the promoter.

It is preferred that the optimised HGSNAT nucleic acid sequence is incorporated into an adeno associated viral (AAV) vector. It is most preferred that the AAV vector is serotype AAV2 True Type or AAV9 or RH10 or AAV8. The inventors have unexpectedly found that serotype AAV2 True Type, AAV9 and RH10 vectors are particularly effective for the delivery of the optimised HGSNAT sequence into the brain for the treatment of MPSIIIC. Most AAVs bind to Heparan sulphate, but it is believed that both AAV9, AAV2 TrueType and potentially RH10 and AAV8 have different binding ligands. The enhanced efficacy in the brain of using AAV9 was unexpected. The efficacy of the AAV2 TrueType result was also unexpected as AAV2 (the main serotype from which TrueType is derived) is regarded as not very effective in the brain. Recent research has suggested that AAV8 confers enhanced neonatal intracranial transduction for potential treatments of MPS IIIB (Gilkes, J. A. et. al., (2016) Gene Therapy, 23, 263-271) and therefore the inventors believe that AAV8 may also be a suitable vector for the optimised HGSNAT nucleic acid sequence.

The serotype AAV2 True Type is preferably a recombinant AAV vector comprising a variant AAV2 caspid protein having a number of amino acid substitutions. Such a recombinant AAV vector is described in detail in WO2015/121501.

The variant AAV2 capsid protein will preferably comprise at least four amino acid substitutions with respect to a wild type AAV2 capsid protein, wherein the at least four amino acid substitutions are present at the following positions in an AAV2 capsid protein sequence: 457, 492, 499 and 533.

The variant AAV2 capsid protein may comprise a sequence of SEQ ID No. 2, or a sequence having at least 95%, at least 96%, at least 97%, at least 98% or at least 99% sequence identity thereto. Alternatively, a wild type AAV2 capsid protein comprising the sequence of SEQ ID No. 3 may be employed.

The variant AAV2 capsid protein may comprise one or more of the following residues: M457, A492, D499 and Y533. In a preferred embodiment, the variant AAV2 capsid protein comprises one or more of the following amino acid substitutions with respect to a wild type AAV2 capsid protein: Q457M, S492A, E499D and F533Y.

In one embodiment, the variant AAV2 capsid protein further comprises one or more amino acid substitutions with respect to the wild type AAV capsid protein at the following positions in the AAV2 capsid protein sequence: 125, 151, 162 and 205. In a preferred embodiment, the variant AAV2 capsid protein comprises one or more of one or more of the following residues: I125, A151, S162 and S205. In another preferred embodiment, the variant AAV2 capsid protein comprises one or more of the following amino acid substitutions with respect to a wild type AAV2 capsid protein: V125I, V151A, A162S and T205S.

In one embodiment, the variant AAV2 capsid protein further comprises one or more amino acid substitutions with respect to the wild type AAV2 capsid protein at the following positions in the AAV2 capsid protein sequence: 585 and 588. Preferably the variant AAV2 capsid protein comprises one or more of one or more of the following residues: S585 and T588. More preferably the variant AAV2 capsid protein comprises one or more of the following amino acid substitutions with respect to a wild type AAV2 capsid protein: R585S and R588T.

In one embodiment, the variant AAV2 capsid protein further comprises one or more amino acid substitutions with respect to the wild type AAV capsid protein at the following positions in the AAV2 capsid protein sequence: 546, 548 and 593. Preferably the variant AAV2 capsid protein comprises one or more of one or more of the following residues: D546, G548, and S593. More preferably the variant AAV2 capsid protein comprises one or more of the following amino acid substitutions with respect to a wild type AAV2 capsid protein: G546D, E548G and A593S.

In one embodiment, the variant AAV2 capsid protein comprises the residue N312, i.e. the residue which is present in the wild type AAV2 capsid protein at position 312. In this embodiment, the variant AAV2 capsid protein is not mutated at position 312 compared to the wild type AAV2 capsid protein sequence.

In one embodiment, the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In one embodiment, the variant AAV2 capsid protein comprises one or more of the following residues: I125, A151, S162, S205, S312, M457, A492, D499, Y533, D546, G548, S585, T588 and/or S593. In a preferred embodiment, the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

In one embodiment, the vector comprises a variant AAV9 capsid protein. In this embodiment, the variant AAV capsid protein may comprise a sequence having at least 95%, at least 96%, at least 97%, at least 98% or at least 99% sequence identity to SEQ ID No. 4.

In another embodiment, the AAV capsid protein is a wild type from AAV9. In this embodiment, the wild type AAV capsid protein comprises the sequence of SEQ ID No. 4.

In one embodiment, at least one amino acid substitution is present at one or more of the following positions in the AAV9 capsid protein sequence: 125, 151, 162, 205, 314, 458, 493, 500, 534, 547, 549, 586, 589 and/or 594. In a preferred embodiment, the variant AAV9 capsid protein comprises one or more of the following amino acid substitutions with respect to a wild type AAV9 capsid protein: L125I, Q151A, N314S, Q458M, V493A, E500D, F534Y, G547D, A589T and/or G594S. In an alternative embodiment, the variant AAV9 capsid protein comprises one or more of the following amino acid substitutions with respect to a wild type AAV9 capsid protein: S162A, 5205T, G549E and/or S586R.

In another embodiment, the vector comprises RH10 capsid protein (SEQ ID No. 5). In another embodiment, the vector comprises a RH10 variant AAV capsid protein comprising a sequence having at least 95%, at least 96%, at least 97%, at least 98% or at least 99% sequence identity to SEQ ID No. 5.

The variant RH10 capsid protein may comprise at least one amino acid substitution at one or more of the following positions in the RH10 capsid protein sequence: 125, 151, 163, 206, 315, 460, 495, 502, 536, 549, 551, 588, 591 and/or 596. These positions in RH10 capsid protein VPI correspond to those disclosed above in relation to AAV2.

Preferably the variant RH10 capsid protein has at least 70%, at least 80%, at least 90%, at least 95%, at least 96%, at least 97%, at least 98% or at least 99% sequence identity to SEQ ID No. 5.

Wild type RH10 capsid protein VPI already contains the following residue at a position which corresponds to an amino acid residue which is present in the variant AAV2 capsid protein disclosed above (SEQ ID No. 2), but not wild type AAV2 (SEQ ID NO: 3): G551 (aligns with G548 in True Type AAV2). Accordingly, in a preferred embodiment, the variant RH10 capsid protein comprises one or more of the following amino acid substitutions with respect to a wild type RH10 capsid protein: V125I, Q151A, K163S, A206S, N315S, T460M, L495A, N502D, F536Y, G549D, Q588S, A591T and/or G596S. Typically such a variant RH10 capsid protein may share one or more functional properties with the variant AAV2 capsid protein (SEQ ID No. 2), e.g. may confer increased infectivity and/or transduction of neuronal tissue compared to wild type RH10 capsid protein.

In alternative embodiments, the variant RH10 capsid protein comprises an amino acid substitution which corresponds to a reversion of a mutations present in True Type AAV2 back to the wild type AAV2 sequence. For instance, the variant RH10 capsid protein may comprise the following substitution: G551E. Typically such a variant RH10 capsid protein may share one or more functional properties with the wild type AAV2 capsid protein (SEQ ID No. 3), e.g. may confer reduced infectivity and/or transduction of neuronal tissue compared to wild type RH10 capsid protein.

In another embodiment, the vector comprises AAV8 capsid protein (SEQ ID No. 6). In another embodiment, the vector comprises a variant AAV8 capsid protein comprising a sequence having at least 95%, at least 96%, at least 97%, at least 98% or at least 99% sequence identity to SEQ ID No. 6.

The variant AAV8 capsid protein may comprise at least one amino acid substitution at one or more of the following positions in the AAV8 capsid protein sequence: 125, 151, 163, 206, 315, 460, 495, 502, 536, 549, 551, 588, 591 and/or 596. These positions in AAV8 capsid protein VP1 correspond to those disclosed above in relation to AAV2.

Preferably the variant AAV8 capsid protein has at least 70%, at least 80%, at least 90%, at least 95%, at least 96%, at least 97%, at least 98% or at least 99% sequence identity to SEQ ID No. 6.

Wild type AAV8 capsid protein VP1 already contains the following residues at positions which correspond to amino acid residues which are present in the variant AAV2 capsid protein disclosed above (SEQ ID No. 2), but not wild type AAV2 (SEQ ID No. 3): S315; T591. Accordingly, in a preferred embodiment, the variant AAV8 capsid protein comprises one or more of the following amino acid substitutions with respect to a wild type AAV8 capsid protein: V125I, Q151A, K163S, A206S, T460M, T495A, N502D, F536Y, N549D, A551G, Q588S and/or G596S. Typically such a variant AAV8 capsid protein may share one or more functional properties with the variant AAV2 capsid protein (SEQ ID No. 2), e.g. may confer increased infectivity and/or transduction of neuronal tissue compared to wild type AAV8 capsid protein.

In alternative embodiments, the variant AAV8 capsid protein comprises one or more amino acid substitutions which correspond to reversions of mutations present in True Type AAV2 back to the wild type AAV2 sequence. For instance, the variant AAV8 capsid protein may comprise one or more of the following substitutions: S315N and/or T591R. Typically such a variant AAV8 capsid protein may share one or more functional properties with the wild type AAV2 capsid protein (SEQ ID No. 3), e.g. may confer reduced infectivity and/or transduction of neuronal of retinal tissue compared to wild type AAV8 capsid protein.

AAV is a helper dependent parvovirus with a single genome (~4.7 kb) including two inverted terminal repeats (ITRs) which contain cis-elements required for replication and packaging. The ITR flanks genes for two different proteins, the first Rep, which is responsible for replication and rescue of the virus. The second, Cap, is a structural protein that produces the capsid that houses the viral genome. Both the Rep and Cap genes are removed from the vector and provided in trans. It requires the help of a helper virus i.e. adenovirus for production to occur. AAV can infect both dividing and non-dividing cells therefore making it a good candidate for delivery of therapeutic genes to the CNS. It can target many different tissue types and different serotypes have different tissue tropism due to changes in their capsid proteins. For example, AAV2, 5, 7, 8, 9 and Rh10 can transduce the CNS with AAV9 and Rh10 as the superior candidates.

The recombinant adeno-associated viral vector (rAAV2) backbone may carry the optimised HGSNAT transgene under the CMV enhancer/chicken β-actin-(CAG) promoter. The rAAV genome encapsulated within serotype 9 capsids can be easily delivered intracerebrally into the CNS via stereotaxic surgery.

A number of vector backbones may be employed. It is preferred that the vector backbone comprises a pTR-UF-11 vector backbone. Such a vector backbone may comprise AAV2 ITRS. Alternative backbones may comprise pSUB201 or pD10 or those available as part of AAV production kits, such as pAAV-CMV (Clontech) and pAAV.MCS (Cell Biolabs).

Choice of promoter can also be critical for efficient transduction of cells. The present inventors chose the ubiquitous CAG promoter because of its ability to transduce many different cell types. This is particularly important in the context of MPSIIIC as the enzyme cannot cross-correct, therefore, the maximum number of cells needed to be transduced, and by choosing the CAG promoter it enable this to be achieved. A number of different clinical trials have used this promotor successfully.

The AAV vector backbone preferred by the inventors was the pTR-UF-11 vector backbone, currently used as the FDA AAV vector reference standard. PTR-UF-11 is derived from pSM620 in which the internal AAV sequences have been replaced by a green fluorescent protein (GFP) gene under the control of a CAG promoter and the SV40 polyadenylation signal followed by the neomycin-resistance gene under the control of the mutant polyoma virus enhancer/promoter (PYF441) and the human bovine growth hormone (BGH) poly(A) site. It is preferably flanked by inverted terminal repeats (ITRs) and contains the cis acting elements from AAV2. HGSNAT is preferably codon optimised by improving the codon usage in the human HGSNAT cDNA to codons most common in human cells, removal of secondary structures and hairpins in mRNA where possible, and insertion of a Kozak sequence at the ATG start site to improve transcription. Codon optimised HGSNAT was inserted into the Sbfl and Sphl sites in pTRUF11.

The composition may be for use in the treatment of a disease or condition attributable to heparin-α-glucosaminide N-acetyltransferase (HGSNAT) deficiency. Alternatively or additionally, the composition may be used in a method of treating a disease or condition attributable to heparin-α-glucosaminide N-acetyltransferase (HGSNAT) deficiency. Yet further alternatively or additionally, the composition may be for use in the manufacture of a medicament for treating a disease or condition attributable to heparin-α-glucosaminide N-acetyltransferase (HGSNAT) deficiency. Such a disease or condition will preferably comprise mucopolysaccharidosis (MPS) IIIC. It is envisaged that the treatment will be performed intracranially by one or more stereotaxic injections, typically injecting around 60 µl at each site of vector at 1×10E12 vg/ml in PBS. It is preferred that the treatment is performed intracranially using up to about 16 stereotaxic injections.

The composition may be a liquid or a solid, for example a powder, gel, or paste. Preferably, a composition is a liquid, preferably an injectable liquid. Such an injectable liquid will preferably be suitable for intracranial administration. The composition may also comprise one or more excipients and such excipients will be known to persons skilled in the art.

The composition may incorporate or be administered in conjunction (either sequentially or simultaneously) with a immunosuppressant. Such immunosuppressants may be selected from one or more of the following: tacrolimus, mycofenolate mofetil and prednisolone. The skilled addressee will understand that other immunosuppressants may also be employed.

In accordance with a further aspect of the present invention, there is provided an adeno associated viral (AAV) vector comprising an optimised HGSNAT nucleic acid sequence of SEQ ID No. 1 or a derivative sequence having at least 77% homology thereof.

The sequence may be a derivative sequence having at least 78% homology with SEQ ID No. 1. More preferred, the derivative sequence has at least 80%, at least 85% or at least 90% homology with SEQ ID No. 1. Even more preferred, the sequence may be a derivative sequence having at least 95%, at least 96%, at least 97%, at least 98% or at least 99% homology with SEQ ID No. 1.

It is preferred that the vector comprises AAV9 or a AAV2 True Type or a RH10 or a AAV8 serotype. The serotype AAV2 True Type is preferably a recombinant AAV vector comprising a variant AAV2 caspid protein having a number of amino acid substitutions.

The variant AAV2 capsid protein will preferably comprise at least four amino acid substitutions with respect to a wild type AAV2 capsid protein, wherein the at least four amino acid substitutions are present at the following positions in an AAV2 capsid protein sequence: 457, 492, 499 and 533.

The variant AAV2 capsid protein may comprise a sequence of SEQ ID No. 2, or a sequence having at least 95%, at least 96%, at least 97%, at least 98% or at least 99% sequence identity thereto. Alternatively, a wild type AAV2 capsid protein comprising the sequence of SEQ ID No. 3 may be employed.

The variant AAV2 capsid protein may comprise one or more of the following residues: M457, A492, D499 and Y533. In a preferred embodiment, the variant AAV2 capsid protein comprises one or more of the following amino acid substitutions with respect to a wild type AAV2 capsid protein: Q457M, S492A, E499D and F533Y.

In one embodiment, the variant AAV2 capsid protein further comprises one or more amino acid substitutions with respect to the wild type AAV capsid protein at the following positions in the AAV2 capsid protein sequence: 125, 151, 162 and 205. In a preferred embodiment, the variant AAV2 capsid protein comprises one or more of one or more of the following residues: I125, A151, S162 and S205. In another preferred embodiment, the variant AAV2 capsid protein comprises one or more of the following amino acid substitutions with respect to a wild type AAV2 capsid protein: V125I, V151A, A162S and T205S.

In one embodiment, the variant AAV2 capsid protein further comprises one or more amino acid substitutions with respect to the wild type AAV2 capsid protein at the following positions in the AAV2 capsid protein sequence: 585 and 588. Preferably the variant AAV2 capsid protein comprises one or more of one or more of the following residues: S585 and T588. More preferably the variant AAV2 capsid protein comprises one or more of the following amino acid substitutions with respect to a wild type AAV2 capsid protein: R585S and R588T.

In one embodiment, the variant AAV2 capsid protein further comprises one or more amino acid substitutions with respect to the wild type AAV capsid protein at the following positions in the AAV2 capsid protein sequence: 546, 548 and 593. Preferably the variant AAV2 capsid protein comprises one or more of one or more of the following residues: D546, G548, and S593. More preferably the variant AAV2 capsid protein comprises one or more of the following amino acid substitutions with respect to a wild type AAV2 capsid protein:
G546D, E548G and A593S.

In one embodiment, the variant AAV2 capsid protein comprises the residue N312, i.e. the residue which is present in the wild type AAV2 capsid protein at position 312. In this embodiment, the variant AAV2 capsid protein is not mutated at position 312 compared to the wild type AAV2 capsid protein sequence.

In one embodiment, the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In one embodiment, the variant AAV2 capsid protein comprises one or more of the following residues: I125, A151, S162, S205, S312, M457, A492, D499, Y533, D546, G548, S585, T588 and/or S593. In a preferred embodiment, the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

In one embodiment, the vector comprises a variant AAV9 capsid protein. In another embodiment, the variant AAV capsid protein comprises a sequence having at least 95%, at least 96%, at least 97%, at least 98% or at least 99% sequence identity to SEQ ID No. 4. In another embodiment, the AAV capsid protein is a wild type from AAV9. In another embodiment, the wild type AAV capsid protein comprises a sequence of SEQ ID No. 4.

In one embodiment, at least one amino acid substitution is present at one or more of the following positions in the AAV9 capsid protein sequence: 125, 151, 162, 205, 314, 458, 493, 500, 534, 547, 549, 586, 589 and/or 594. In a preferred embodiment, the variant AAV9 capsid protein comprises one or more of the following amino acid substitutions with respect to a wild type AAV9 capsid protein: L125I, Q151A, N3145, Q458M, V493A, E500D, F534Y, G547D, A589T and/or G594S. In an alternative embodiment, the variant AAV9 capsid protein comprises one or more of the following amino acid substitutions with respect to a wild type AAV9 capsid protein: S162A, 5205T, G549E and/or S586R.

In another embodiment, the vector comprises RH10 capsid protein (SEQ ID No. 5). In another embodiment, the variant AAV capsid protein comprises a sequence having at least 95%, at least 96%, at least 97%, at least 98% or at least 99% sequence identity to SEQ ID No. 5.

The variant RH10 capsid protein may comprise at least one amino acid substitution at one or more of the following positions in the RH10 capsid protein sequence: 125, 151, 163, 206, 315, 460, 495, 502, 536, 549, 551, 588, 591 and/or 596. These positions in RH10 capsid protein VP1 correspond to those disclosed above in relation to AAV2.

Preferably the variant RH10 capsid protein has at least 70%, at least 80%, at least 90%, at least 95%, at least 96%, at least 97%, at least 98% or at least 99% sequence identity to SEQ ID No. 5.

Wild type RH10 capsid protein VP1 already contains the following residue at a position which corresponds to an amino acid residue which is present in the variant AAV2 capsid protein disclosed above (SEQ ID No. 2), but not wild type AAV2 (SEQ ID NO: 3): G551 (aligns with G548 in True Type AAV2). Accordingly, in a preferred embodiment, the variant RH10 capsid protein comprises one or more of the following amino acid substitutions with respect to a wild type RH10 capsid protein: V125I, Q151A, K163S, A206S, N315S, T460M, L495A, N502D, F536Y, G549D, Q588S, A591T and/or G596S. Typically such a variant RH10 capsid protein may share one or more functional properties with the variant AAV2 capsid protein (SEQ ID No. 2), e.g. may confer increased infectivity and/or transduction of neuronal tissue compared to wild type RH10 capsid protein.

In alternative embodiments, the variant RH10 capsid protein comprises an amino acid substitution which corresponds to a reversion of a mutations present in True Type AAV2 back to the wild type AAV2 sequence. For instance, the variant RH10 capsid protein may comprise the following substitution: G551E. Typically such a variant RH10 capsid protein may share one or more functional properties with the wild type AAV2 capsid protein (SEQ ID No. 3), e.g. may confer reduced infectivity and/or transduction of neuronal tissue compared to wild type RH10 capsid protein.

In another embodiment, the vector comprises AAV8 capsid protein (SEQ ID No. 6). In another embodiment, the vector comprises a variant AAV8 capsid protein comprising a sequence having at least 95%, at least 96%, at least 97%, at least 98% or at least 99% sequence identity to SEQ ID No. 6.

The variant AAV8 capsid protein may comprise at least one amino acid substitution at one or more of the following positions in the AAV8 capsid protein sequence: 125, 151, 163, 206, 315, 460, 495, 502, 536, 549, 551, 588, 591 and/or 596. These positions in AAV8 capsid protein VP1 correspond to those disclosed above in relation to AAV2.

Preferably the variant AAV8 capsid protein has at least 70%, at least 80%, at least 90%, at least 95%, at least 96%, at least 97%, at least 98% or at least 99% sequence identity to SEQ ID No. 6.

Wild type AAV8 capsid protein VP1 already contains the following residues at positions which correspond to amino acid residues which are present in the variant AAV2 capsid protein disclosed above (SEQ ID No. 2), but not wild type AAV2 (SEQ ID No. 3): S315; T591. Accordingly, in a preferred embodiment, the variant AAV8 capsid protein comprises one or more of the following amino acid substitutions with respect to a wild type AAV8 capsid protein: V125I, Q151A, K163S, A206S, T460M, T495A, N502D, F536Y, N549D, A551G, Q588S and/or G596S. Typically such a variant AAV8 capsid protein may share one or more functional properties with the variant AAV2 capsid protein (SEQ ID No. 2), e.g. may confer increased infectivity and/or transduction of neuronal tissue compared to wild type AAV8 capsid protein.

In alternative embodiments, the variant AAV8 capsid protein comprises one or more amino acid substitutions which correspond to reversions of mutations present in True Type AAV2 back to the wild type AAV2 sequence. For instance, the variant AAV8 capsid protein may comprise one or more of the following substitutions: S315N and/or T591R. Typically such a variant AAV8 capsid protein may share one or more functional properties with the wild type AAV2 capsid protein (SEQ ID No. 3), e.g. may confer reduced infectivity and/or transduction of neuronal of retinal tissue compared to wild type AAV8 capsid protein.

In common with the first aspect of the invention, the optimised HGSNAT nucleic acid sequence may be under the control of a CAG promoter. The optimised HGSNAT nucleic acid sequence may also be flanked by inverted terminal repeats and contains the cis acting elements from adeno associated virus 2 (AAV2). The optimised HGSNAT nucleic acid sequence may be codon optimised by selecting codons most common in human cells and/or reducing one or more secondary structures and hairpins which may form in subsequent mRNA and/or inserting a Kozak sequence at the ATG start site. The vector backbone may comprise the pTR-UF-11 vector backbone.

It is envisaged that the vector would be for use in the treatment of a disease or condition attributable to heparin-α-glucosaminide N-acetyltransferase (HGSNAT) deficiency. Alternatively or additionally, the vector may be used in a method of treating a disease or condition attributable to heparin-α-glucosaminide N-acetyltransferase (HGSNAT) deficiency. Yet further alternatively or additionally, the vector may be for use in the manufacture of a medicament for treating a disease or condition attributable to heparin-α-glucosaminide N-acetyltransferase (HGSNAT) deficiency. Such a disease or condition will preferably comprise mucopolysaccharidosis (MPS) IIIC. Again, it is envisaged that the treatment will be performed intracranially by stereotaxic injections.

In accordance with a yet further aspect of the present invention, there is provided use of an adeno associated viral (AAV) vector having a AAV9, AAV2 True Type, RH10 or AAV8 serotype for intracranial delivery of therapeutic nucleic acid sequence for the treatment of a disease or condition affecting the brain of an individual.

It is preferred that the therapeutic nucleic acid sequence comprises an optimised HGSNAT nucleic acid sequence as herein above described with reference to the first aspect of the invention.

The variant AAV2 capsid protein will preferably comprise at least four amino acid substitutions with respect to a wild type AAV2 capsid protein, wherein the at least four amino acid substitutions are present at the following positions in an AAV2 capsid protein sequence: 457, 492, 499 and 533.

The variant AAV2 capsid protein may comprise a sequence of SEQ ID No. 2, or a sequence having at least 95%, at least 96%, at least 97%, at least 98% or at least 99% sequence identity thereto. Alternatively, a wild type AAV2 capsid protein comprising the sequence of SEQ ID No. 3 may be employed.

The variant AAV2 capsid protein may comprise one or more of the following residues: M457, A492, D499 and Y533. In a preferred embodiment, the variant AAV2 capsid protein comprises one or more of the following amino acid substitutions with respect to a wild type AAV2 capsid protein: Q457M, S492A, E499D and F533Y.

In one embodiment, the variant AAV2 capsid protein further comprises one or more amino acid substitutions with respect to the wild type AAV capsid protein at the following positions in the AAV2 capsid protein sequence: 125, 151, 162 and 205. In a preferred embodiment, the variant AAV2 capsid protein comprises one or more of one or more of the following residues: I125, A151, S162 and S205. In another preferred embodiment, the variant AAV2 capsid protein comprises one or more of the following amino acid substitutions with respect to a wild type AAV2 capsid protein: V125I, V151A, A162S and T205S.

In one embodiment, the variant AAV2 capsid protein further comprises one or more amino acid substitutions with respect to the wild type AAV2 capsid protein at the following positions in the AAV2 capsid protein sequence: 585 and 588. Preferably the variant AAV2 capsid protein comprises one or more of one or more of the following residues: S585 and T588. More preferably the variant AAV2 capsid protein comprises one or more of the following amino acid substitutions with respect to a wild type AAV2 capsid protein: R585S and R588T.

In one embodiment, the variant AAV2 capsid protein further comprises one or more amino acid substitutions with respect to the wild type AAV capsid protein at the following positions in the AAV2 capsid protein sequence: 546, 548 and 593. Preferably the variant AAV2 capsid protein comprises one or more of one or more of the following residues: D546, G548, and S593. More preferably the variant AAV2 capsid protein comprises one or more of the following amino acid substitutions with respect to a wild type AAV2 capsid protein: G546D, E548G and A593S.

In one embodiment, the variant AAV2 capsid protein comprises the residue N312, i.e. the residue which is present in the wild type AAV2 capsid protein at position 312. In this embodiment, the variant AAV2 capsid protein is not mutated at position 312 compared to the wild type AAV2 capsid protein sequence.

In one embodiment, the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In one embodiment, the variant AAV2 capsid protein comprises one or more of the following residues: I125, A151, S162, S205, S312, M457, A492, D499, Y533, D546, G548, S585, T588 and/or S593. In a preferred embodiment, the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

In one embodiment, the vector comprises a variant AAV9 capsid protein. In another embodiment, the variant AAV capsid protein comprises a sequence having at least 95%, at least 96%, at least 97%, at least 98% or at least 99% sequence identity to SEQ ID No. 4. In another embodiment, the AAV capsid protein is a wild type from AAV9. In another embodiment, the wild type AAV capsid protein comprises a sequence of SEQ ID No. 4.

In one embodiment, at least one amino acid substitution is present at one or more of the following positions in the AAV9 capsid protein sequence: 125, 151, 162, 205, 314, 458, 493, 500, 534, 547, 549, 586, 589 and/or 594. In a preferred embodiment, the variant AAV9 capsid protein comprises one or more of the following amino acid substitutions with respect to a wild type AAV9 capsid protein: L125I, Q151A, N314S, Q458M, V493A, E500D, F534Y, G547D, A589T and/or G594S. In an alternative embodiment, the variant AAV9 capsid protein comprises one or more of the following amino acid substitutions with respect to a wild type AAV9 capsid protein: S162A, 5205T, G549E and/or S586R.

In another embodiment, the vector comprises RH10 capsid protein (SEQ ID No. 5). In another embodiment, the variant AAV capsid protein comprises a sequence having at least 95%, at least 96%, at least 97%, at least 98% or at least 99% sequence identity to SEQ ID No. 5.

The variant RH10 capsid protein may comprise at least one amino acid substitution at one or more of the following positions in the RH10 capsid protein sequence: 125, 151, 163, 206, 315, 460, 495, 502, 536, 549, 551, 588, 591 and/or 596. These positions in RH10 capsid protein VPI correspond to those disclosed above in relation to AAV2.

Preferably the variant RH10 capsid protein has at least 70%, at least 80%, at least 90%, at least 95%, at least 96%, at least 97%, at least 98% or at least 99% sequence identity to SEQ ID No. 5.

Wild type RH10 capsid protein VPI already contains the following residue at a position which corresponds to an amino acid residue which is present in the variant AAV2 capsid protein disclosed above (SEQ ID No. 2), but not wild type AAV2 (SEQ ID NO: 3): G551 (aligns with G548 in True Type AAV2). Accordingly, in a preferred embodiment, the variant RH10 capsid protein comprises one or more of the following amino acid substitutions with respect to a wild type RH10 capsid protein: V125I, Q151A, K163S, A206S, N315S, T460M, L495A, N502D, F536Y, G549D, Q588S, A591T and/or G596S. Typically such a variant RH10 capsid protein may share one or more functional properties with the variant AAV2 capsid protein (SEQ ID No. 2), e.g. may confer increased infectivity and/or transduction of neuronal tissue compared to wild type RH10 capsid protein.

In alternative embodiments, the variant RH10 capsid protein comprises an amino acid substitution which corresponds to a reversion of a mutations present in True Type AAV2 back to the wild type AAV2 sequence. For instance, the variant RH10 capsid protein may comprise the following substitution: G551E. Typically such a variant RH10 capsid protein may share one or more functional properties with the wild type AAV2 capsid protein (SEQ ID No. 3), e.g. may confer reduced infectivity and/or transduction of neuronal tissue compared to wild type RH10 capsid protein.

In another embodiment, the vector comprises AAV8 capsid protein (SEQ ID No. 6). In another embodiment, the vector comprises a variant AAV8 capsid protein comprising a sequence having at least 95%, at least 96%, at least 97%, at least 98% or at least 99% sequence identity to SEQ ID No. 6.

The variant AAV8 capsid protein may comprise at least one amino acid substitution at one or more of the following positions in the AAV8 capsid protein sequence: 125, 151, 163, 206, 315, 460, 495, 502, 536, 549, 551, 588, 591 and/or 596. These positions in AAV8 capsid protein VP1 correspond to those disclosed above in relation to AAV2.

Preferably the variant AAV8 capsid protein has at least 70%, at least 80%, at least 90%, at least 95%, at least 96%, at least 97%, at least 98% or at least 99% sequence identity to SEQ ID No. 6.

Wild type AAV8 capsid protein VP1 already contains the following residues at positions which correspond to amino acid residues which are present in the variant AAV2 capsid protein disclosed above (SEQ ID No. 2), but not wild type AAV2 (SEQ ID No. 3): S315; T591. Accordingly, in a preferred embodiment, the variant AAV8 capsid protein comprises one or more of the following amino acid substitutions with respect to a wild type AAV8 capsid protein: V125I, Q151A, K163S, A206S, T460M, T495A, N502D, F536Y, N549D, A551G, Q588S and/or G596S. Typically such a variant AAV8 capsid protein may share one or more functional properties with the variant AAV2 capsid protein (SEQ ID No. 2), e.g. may confer increased infectivity and/or transduction of neuronal tissue compared to wild type AAV8 capsid protein.

In alternative embodiments, the variant AAV8 capsid protein comprises one or more amino acid substitutions which correspond to reversions of mutations present in True Type AAV2 back to the wild type AAV2 sequence. For instance, the variant AAV8 capsid protein may comprise one or more of the following substitutions: S315N and/or T591R. Typically such a variant AAV8 capsid protein may share one or more functional properties with the wild type AAV2 capsid protein (SEQ ID No. 3), e.g. may confer reduced infectivity and/or transduction of neuronal of retinal tissue compared to wild type AAV8 capsid protein.

It is preferred that the intracranial delivery is by injection, and in particular stereotaxic injections.

The use of the vector may be for the treatment of a disease or condition attributable to heparin-α-glucosaminide N-acetyltransferase (HGSNAT) deficiency. Alternatively or additionally, the use of the vector may be in a method for treating a disease the composition may be used in a method of treating a disease or condition attributable to heparin-α-glucosaminide N-acetyltransferase (HGSNAT) deficiency. Yet further alternatively or additionally, the use of the vector may be in the manufacture of a medicament for treating a disease or condition attributable to heparin-α-glucosaminide N-acetyltransferase (HGSNAT) deficiency. Diseases or conditions attributable to heparin-α-glucosaminide N-acetyltransferase (HGSNAT) deficiency include mucopolysaccharidosis (MPS) IIIC.

In accordance with a yet further aspect of the present invention, there is provided use of an adeno associated viral (AAV) vector having a AAV9 or AAV2 True Type or RH10 or AAV8 serotype for intracranial delivery of a HGSNAT cDNA nucleic acid sequence.

It is preferred that the optimised HGSNAT nucleic acid sequence is incorporated into an adeno associated viral (AAV) vector.

The variant AAV2 capsid protein will preferably comprise at least four amino acid substitutions with respect to a wild type AAV2 capsid protein, wherein the at least four amino acid substitutions are present at the following positions in an AAV2 capsid protein sequence: 457, 492, 499 and 533.

The variant AAV2 capsid protein may comprise a sequence of SEQ ID No. 2, or a sequence having at least 95%, at least 96%, at least 97%, at least 98% or at least 99% sequence identity thereto. Alternatively, a wild type AAV2 capsid protein comprising the sequence of SEQ ID No. 3 may be employed.

The variant AAV2 capsid protein may comprise one or more of the following residues: M457, A492, D499 and Y533. In a preferred embodiment, the variant AAV2 capsid protein comprises one or more of the following amino acid substitutions with respect to a wild type AAV2 capsid protein: Q457M, S492A, E499D and F533Y.

In one embodiment, the variant AAV2 capsid protein further comprises one or more amino acid substitutions with respect to the wild type AAV capsid protein at the following positions in the AAV2 capsid protein sequence: 125, 151, 162 and 205. In a preferred embodiment, the variant AAV2 capsid protein comprises one or more of one or more of the following residues: I125, A151, S162 and S205. In another preferred embodiment, the variant AAV2 capsid protein comprises one or more of the following amino acid substitutions with respect to a wild type AAV2 capsid protein: V125I, V151A, A162S and T205S.

In one embodiment, the variant AAV2 capsid protein further comprises one or more amino acid substitutions with respect to the wild type AAV2 capsid protein at the following positions in the AAV2 capsid protein sequence: 585 and 588. Preferably the variant AAV2 capsid protein comprises one or more of one or more of the following residues: S585 and T588. More preferably the variant AAV2 capsid protein comprises one or more of the following amino acid substitutions with respect to a wild type AAV2 capsid protein: R585S and R588T.

In one embodiment, the variant AAV2 capsid protein further comprises one or more amino acid substitutions with respect to the wild type AAV capsid protein at the following positions in the AAV2 capsid protein sequence: 546, 548 and 593. Preferably the variant AAV2 capsid protein comprises one or more of one or more of the following residues: D546, G548, and S593. More preferably the variant AAV2 capsid protein comprises one or more of the following amino acid substitutions with respect to a wild type AAV2 capsid protein: G546D, E548G and A593S.

In one embodiment, the variant AAV2 capsid protein comprises the residue N312, i.e. the residue which is present in the wild type AAV2 capsid protein at position 312. In this embodiment, the variant AAV2 capsid protein is not mutated at position 312 compared to the wild type AAV2 capsid protein sequence.

In one embodiment, the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In one embodiment, the variant AAV2 capsid protein comprises one or more of the following residues: I125, A151, S162, S205, S312, M457, A492, D499, Y533, D546, G548, S585, T588 and/or S593. In a preferred embodiment, the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

In one embodiment, the vector comprises a variant AAV9 capsid protein. In another embodiment, the variant AAV capsid protein comprises a sequence having at least 95%, at least 96%, at least 97%, at least 98% or at least 99% sequence identity to SEQ ID No. 4. In another embodiment, the AAV capsid protein is a wild type from AAV9. In another embodiment, the wild type AAV capsid protein comprises a sequence of SEQ ID No. 4.

In one embodiment, at least one amino acid substitution is present at one or more of the following positions in the AAV9 capsid protein sequence: 125, 151, 162, 205, 314, 458, 493, 500, 534, 547, 549, 586, 589 and/or 594. In a preferred embodiment, the variant AAV9 capsid protein comprises one or more of the following amino acid substitutions with respect to a wild type AAV9 capsid protein: L125I, Q151A, N3145, Q458M, V493A, E500D, F534Y, G547D, A589T and/or G594S. In an alternative embodiment, the variant AAV9 capsid protein comprises one or more of the following amino acid substitutions with respect to a wild type AAV9 capsid protein: S162A, 5205T, G549E and/or S586R.

In another embodiment, the vector comprises RH10 capsid protein (SEQ ID No. 5). In another embodiment, the vector comprises a RH10 variant AAV capsid protein comprising a sequence having at least 95%, at least 96%, at least 97%, at least 98% or at least 99% sequence identity to SEQ ID No. 5.

The variant RH10 capsid protein may comprise at least one amino acid substitution at one or more of the following positions in the RH10 capsid protein sequence: 125, 151, 163, 206, 315, 460, 495, 502, 536, 549, 551, 588, 591 and/or 596. These positions in RH10 capsid protein VP1 correspond to those disclosed above in relation to AAV2.

Preferably the variant RH10 capsid protein has at least 70%, at least 80%, at least 90%, at least 95%, at least 96%, at least 97%, at least 98% or at least 99% sequence identity to SEQ ID No. 5.

Wild type RH10 capsid protein VP1 already contains the following residue at a position which corresponds to an amino acid residue which is present in the variant AAV2 capsid protein disclosed above (SEQ ID No. 2), but not wild type AAV2 (SEQ ID NO: 3): G551 (aligns with G548 in True Type AAV2). Accordingly, in a preferred embodiment, the variant RH10 capsid protein comprises one or more of the following amino acid substitutions with respect to a wild type RH10 capsid protein: V125I, Q151A, K163S, A206S, N315S, T460M, L495A, N502D, F536Y, G549D, Q588S, A591T and/or G596S. Typically such a variant RH10 capsid protein may share one or more functional properties with the variant AAV2 capsid protein (SEQ ID No. 2), e.g. may confer increased infectivity and/or transduction of neuronal tissue compared to wild type RH10 capsid protein.

In alternative embodiments, the variant RH10 capsid protein comprises an amino acid substitution which corresponds to a reversion of a mutations present in True Type AAV2 back to the wild type AAV2 sequence. For instance, the variant RH10 capsid protein may comprise the following substitution: G551E. Typically such a variant RH10 capsid protein may share one or more functional properties with the wild type AAV2 capsid protein (SEQ ID No. 3), e.g. may confer reduced infectivity and/or transduction of neuronal tissue compared to wild type RH10 capsid protein.

In another embodiment, the vector comprises AAV8 capsid protein (SEQ ID No. 6). In another embodiment, the vector comprises a variant AAV8 capsid protein comprising a sequence having at least 95%, at least 96%, at least 97%, at least 98% or at least 99% sequence identity to SEQ ID No. 6.

The variant AAV8 capsid protein may comprise at least one amino acid substitution at one or more of the following positions in the AAV8 capsid protein sequence: 125, 151, 163, 206, 315, 460, 495, 502, 536, 549, 551, 588, 591 and/or 596. These positions in AAV8 capsid protein VP1 correspond to those disclosed above in relation to AAV2.

Preferably the variant AAV8 capsid protein has at least 70%, at least 80%, at least 90%, at least 95%, at least 96%, at least 97%, at least 98% or at least 99% sequence identity to SEQ ID No. 6.

Wild type AAV8 capsid protein VP1 already contains the following residues at positions which correspond to amino acid residues which are present in the variant AAV2 capsid protein disclosed above (SEQ ID No. 2), but not wild type AAV2 (SEQ ID No. 3): S315; T591. Accordingly, in a preferred embodiment, the variant AAV8 capsid protein comprises one or more of the following amino acid substitutions with respect to a wild type AAV8 capsid protein: V125I, Q151A, K163S, A206S, T460M, T495A, N502D, F536Y, N549D, A551G, Q588S and/or G596S. Typically such a variant AAV8 capsid protein may share one or more functional properties with the variant AAV2 capsid protein (SEQ ID No. 2), e.g. may confer increased infectivity and/or transduction of neuronal tissue compared to wild type AAV8 capsid protein.

In alternative embodiments, the variant AAV8 capsid protein comprises one or more amino acid substitutions which correspond to reversions of mutations present in True Type AAV2 back to the wild type AAV2 sequence. For instance, the variant AAV8 capsid protein may comprise one or more of the following substitutions: S315N and/or T591R. Typically such a variant AAV8 capsid protein may share one or more functional properties with the wild type AAV2 capsid protein (SEQ ID No. 3), e.g. may confer reduced infectivity and/or transduction of neuronal of retinal tissue compared to wild type AAV8 capsid protein.

The HGSNAT cDNA nucleic acid sequence may comprise an optimised HGSNAT nucleic acid sequence of SEQ ID No. 1 or a derivative sequence having at least 77% homology thereof.

Preferably, the sequence may be a derivative sequence has at least 78% homology with SEQ ID No. 1. More preferred, the derivative sequence has at least 80%, at least 85% or at least 90% homology with SEQ ID No. 1. Even more preferred, the sequence may be a derivative sequence having at least 95%, at least 96%, at least 97%, at least 98% or at least 99% homology with SEQ ID No. 1.

In another aspect of the present invention, there is provided a kit of parts for use in the treatment of an individual suffering from a disease or condition attributable to heparin-α-glucosaminide N-acetyltransferase (HGSNAT) deficiency, the kit comprising:

a) a composition as herein above described with reference to the first aspect or a vector as herein above described with reference to second first aspect; and b) one or more needles or syringes for intracranial administration of the composition or vector.

The composition or vector may be in a buffer solution or other type of solution in order to keep the vector stable and maintain efficacy during storage.

The kit may further comprise a trepanning device for drilling or scraping a hole in the skull of an individual. It may furthermore comprise a needle and optionally a suture.

The kit may further comprise instructions for use, a dosage regimen, one or more solvents and one or more containers if appropriate.

The disease or condition for which the kit is used, is preferably mucopolysaccharidosis (MPS) IIIC.

For all aspects, sequence homology is determined by comparing two aligned substantially complementary sequences over their length and overall homology is expressed as a percentage. The measurement of nucleotide sequence homology is well known in the art, using specialist computer programs such as "BLAST".

Herein reference to "a" or "an" includes within its scope both the singular, and the plural, i.e. one or more.

Unless stated otherwise, the features of each aspect applies to the other aspects of the invention, mutatis mutandis.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

DETAILED DESCRIPTION OF THE INVENTION

Figure 2:
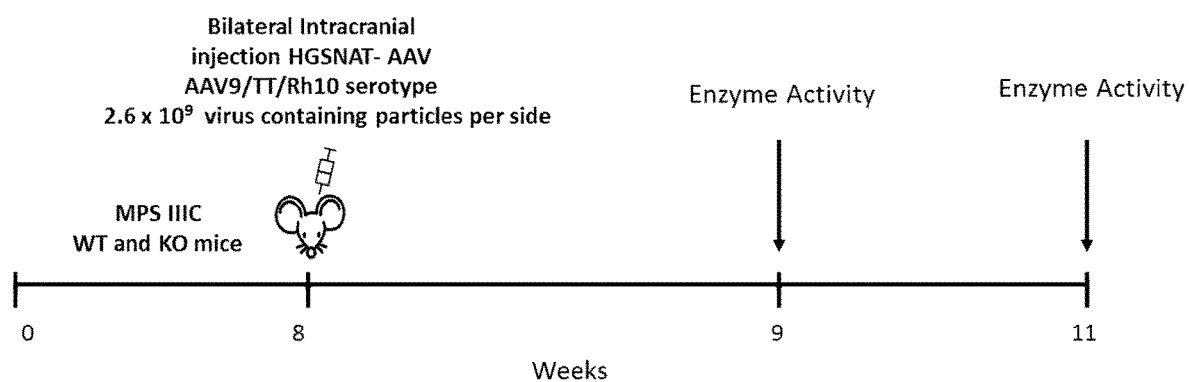
Figure 2:
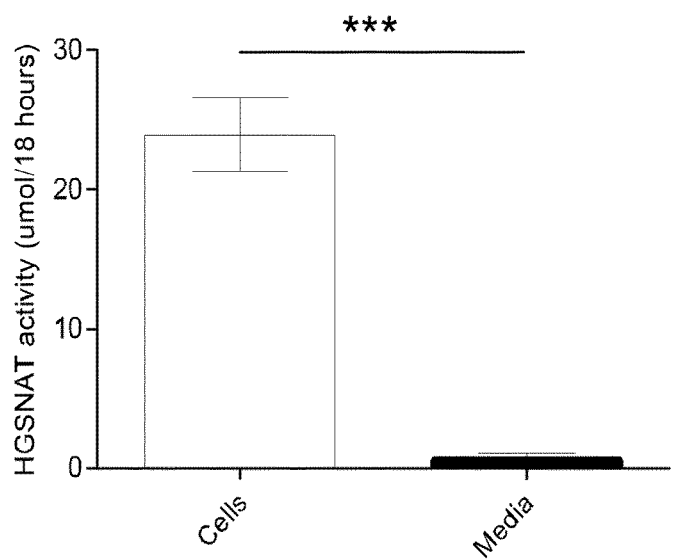
Figure 2:
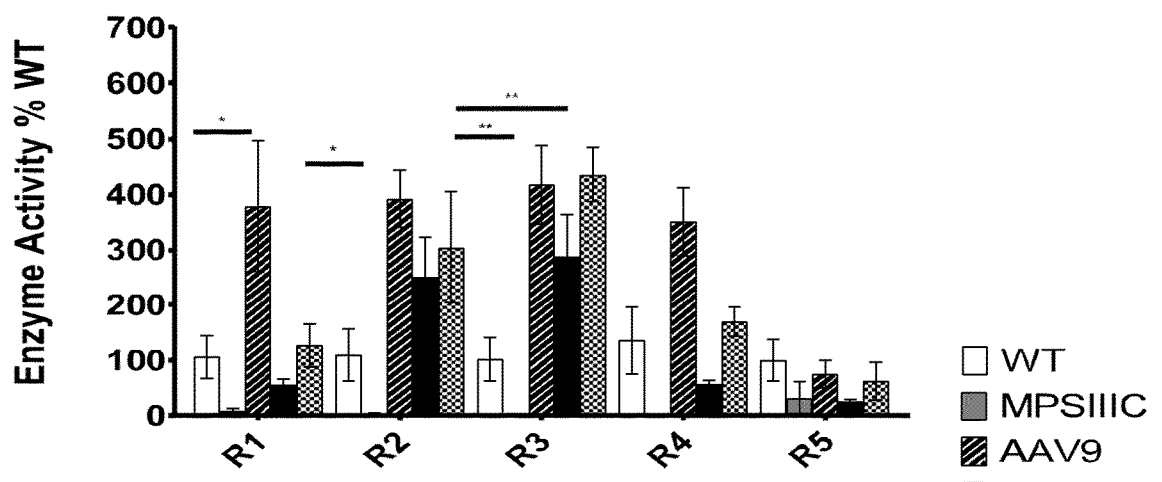
Figure 2:
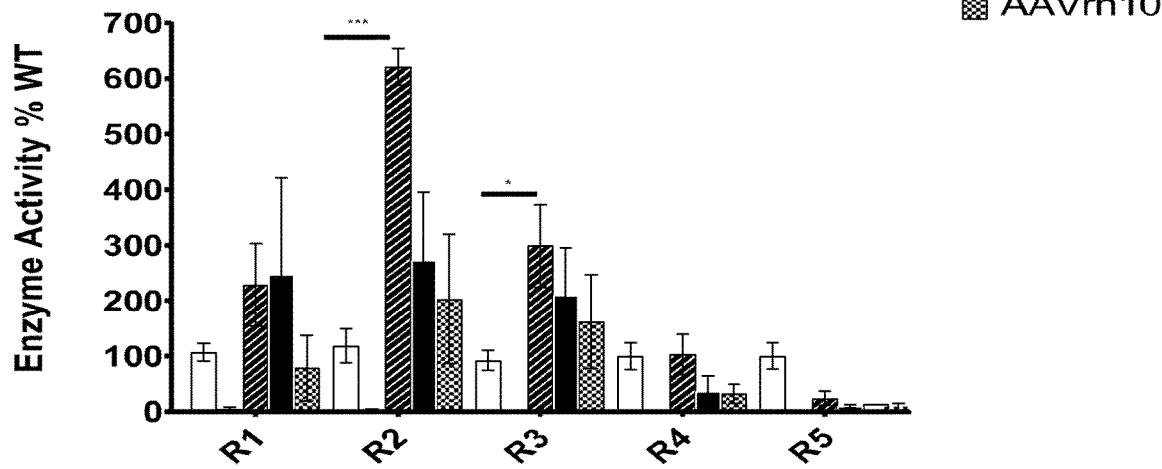
Figure 3:
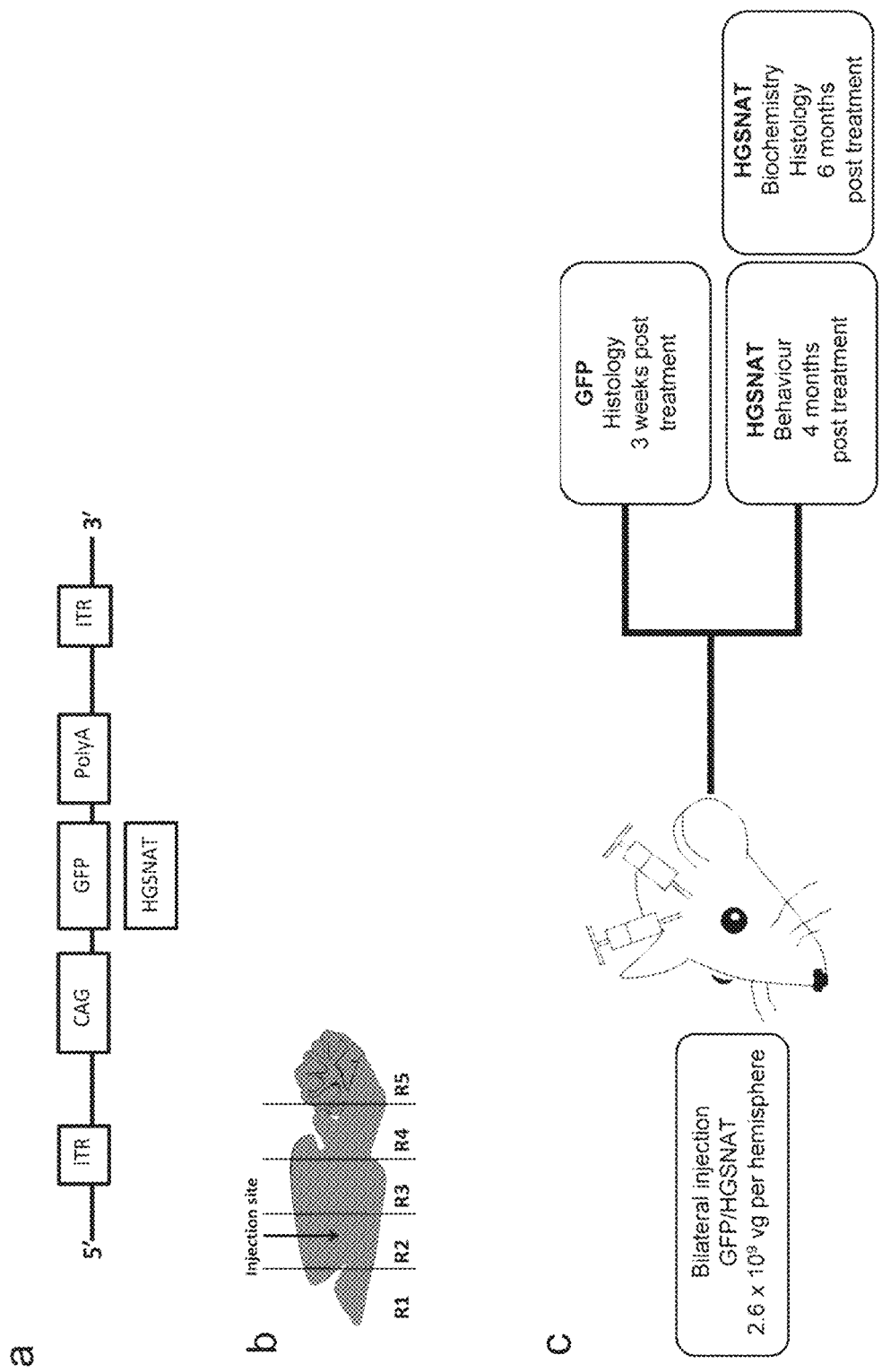
Figure 3:
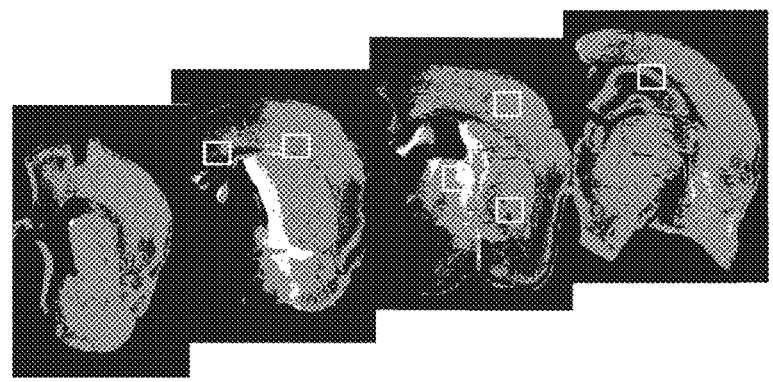
Figure 3:
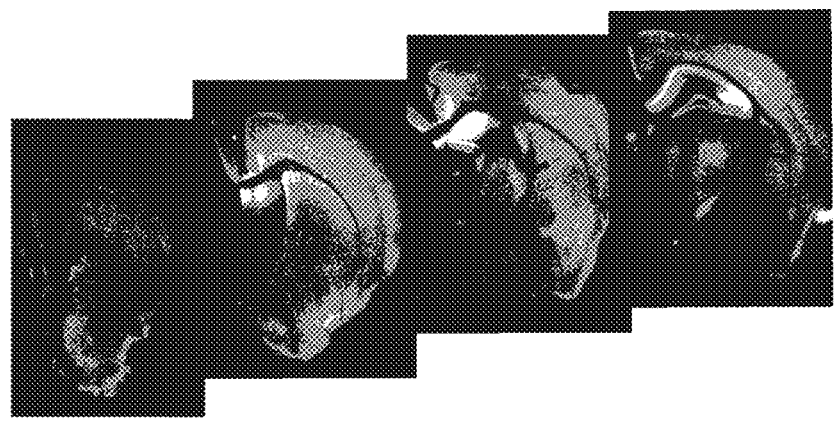
Figure 3:
Figure 3:
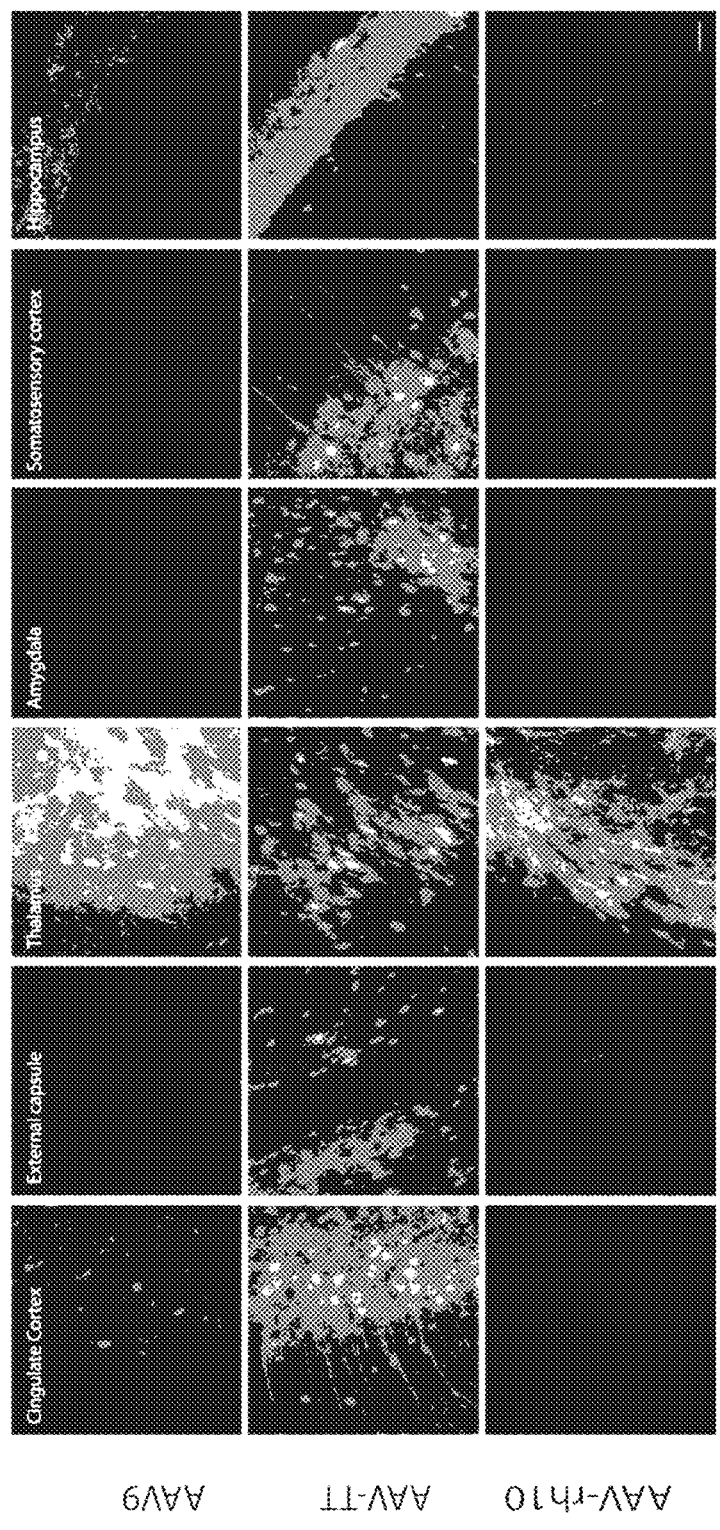
Figure 3:
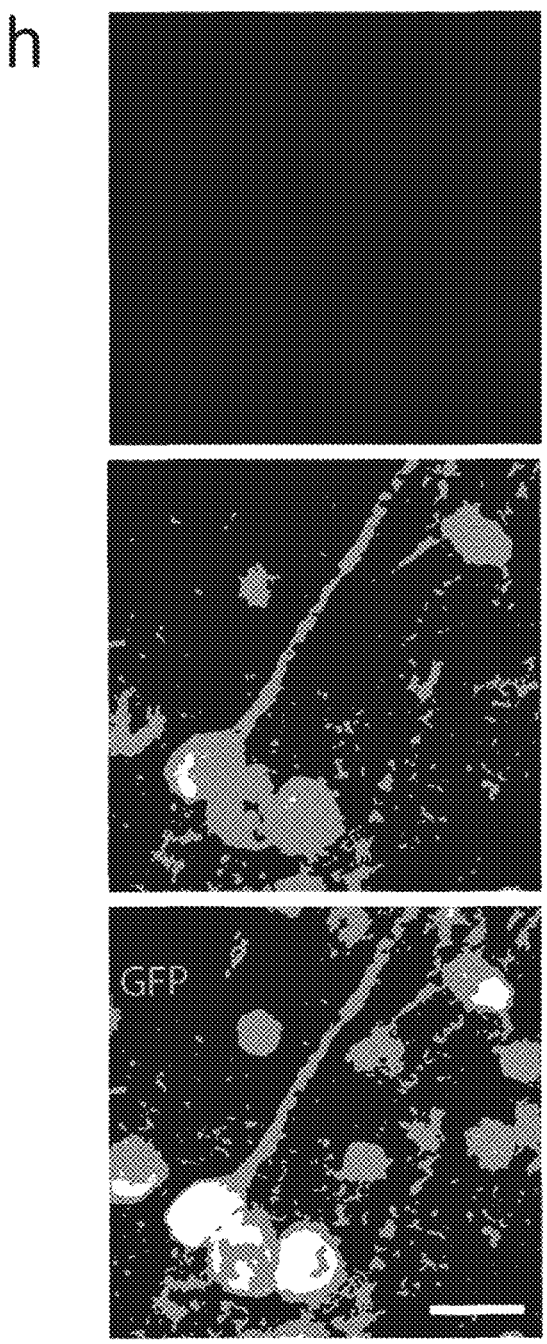
Figure 3:
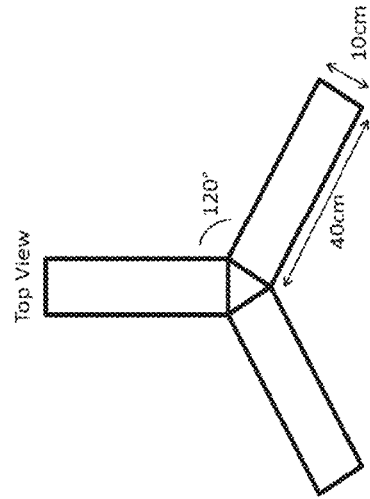
Figure 3:
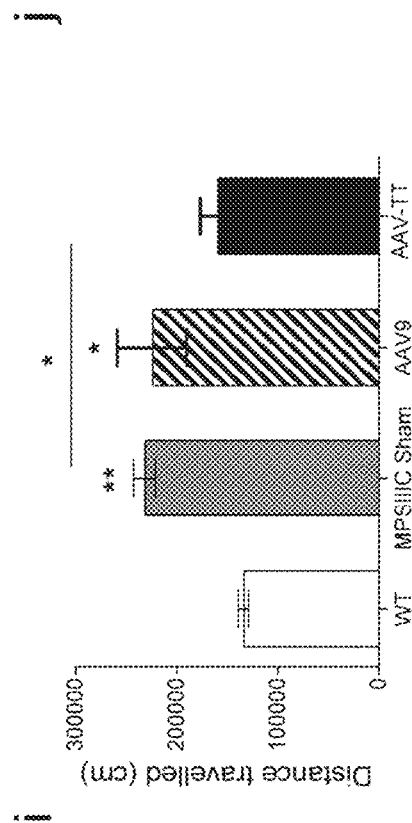
Figure 3:
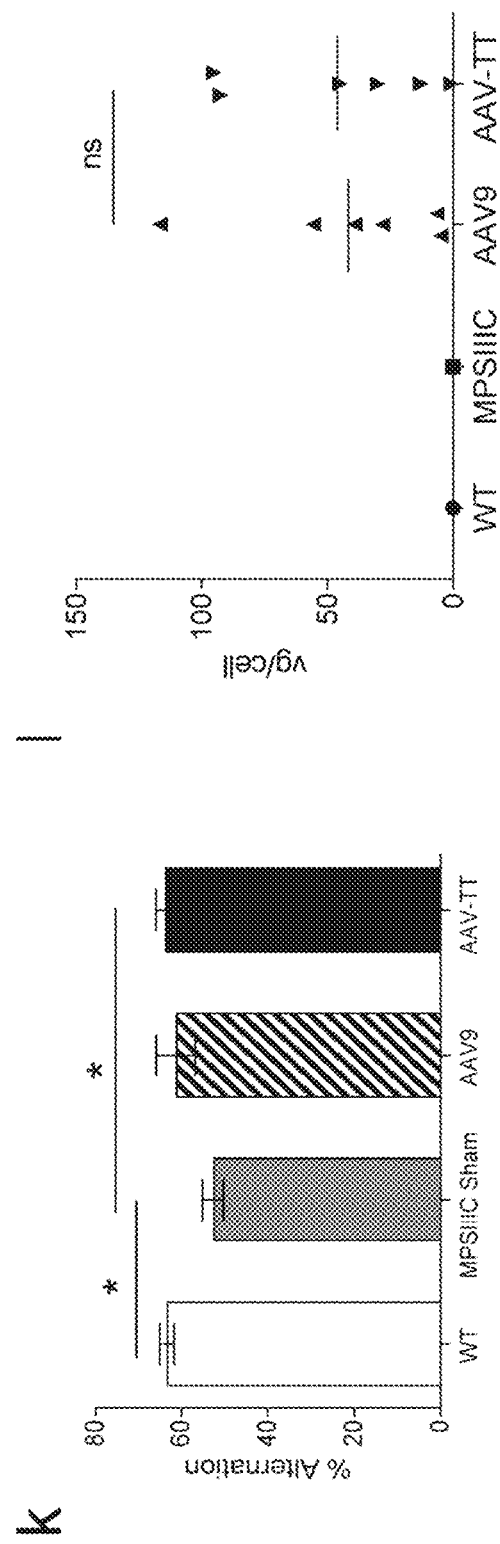
Figure 3:
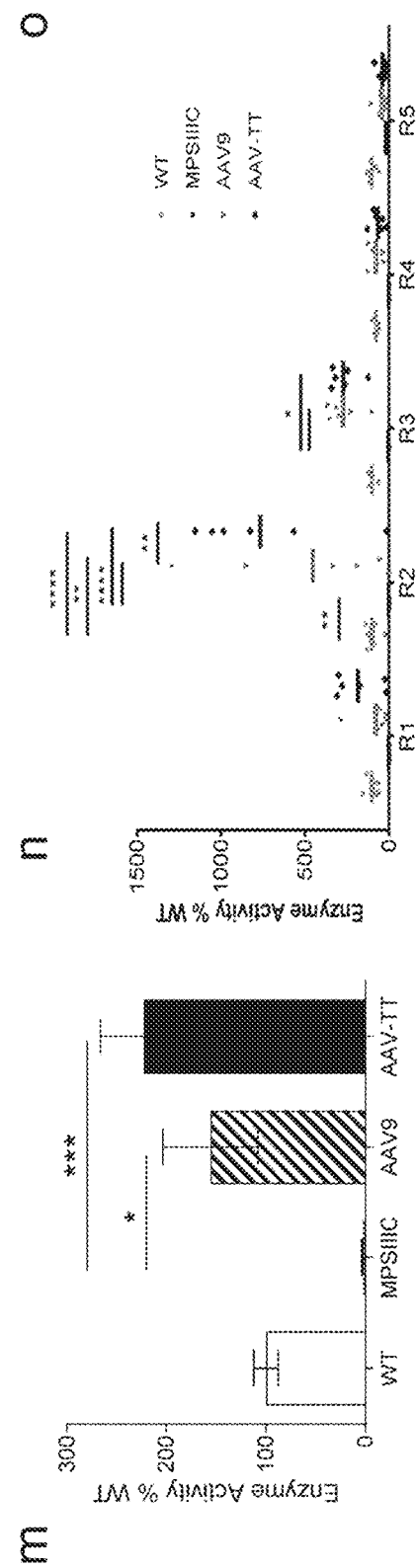
Figure 3:
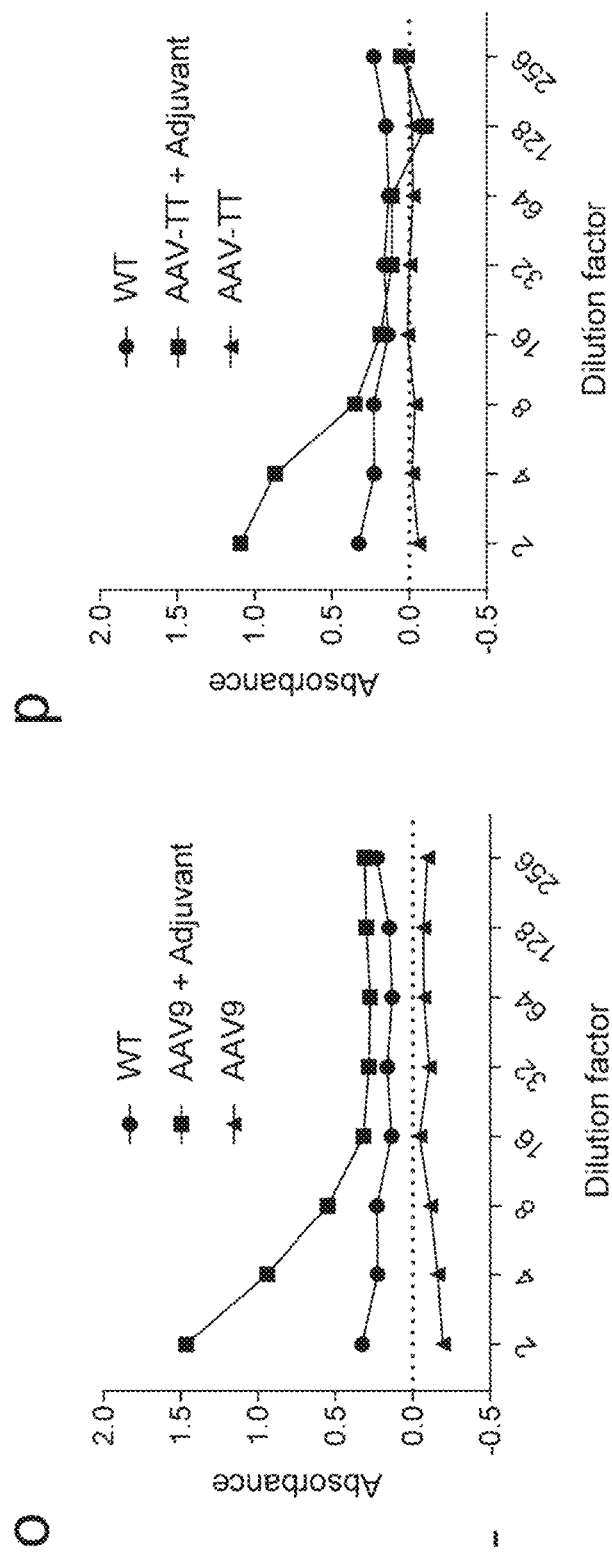
Figure 4:
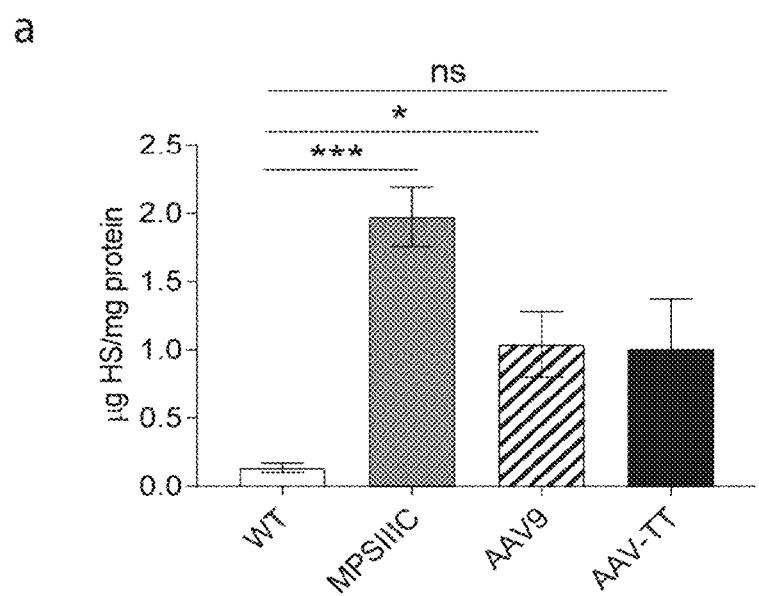
Figure 4:
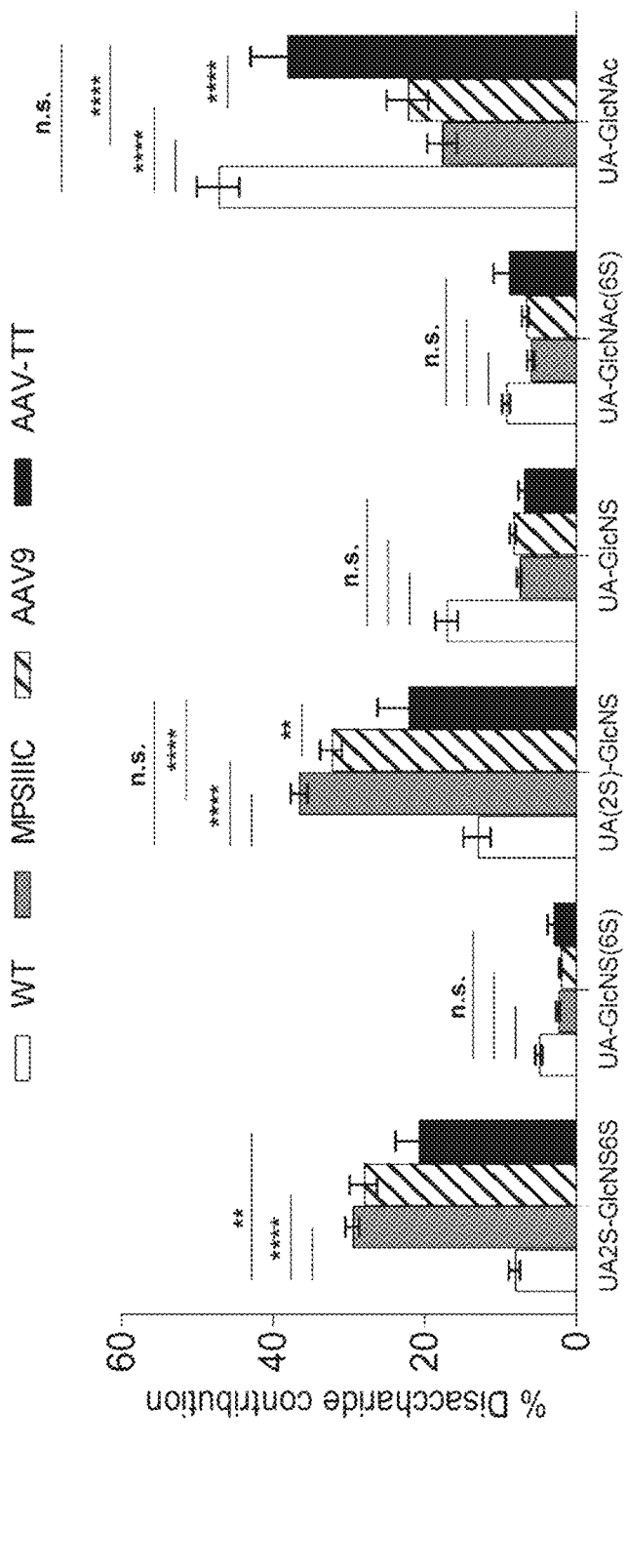
Figure 4:
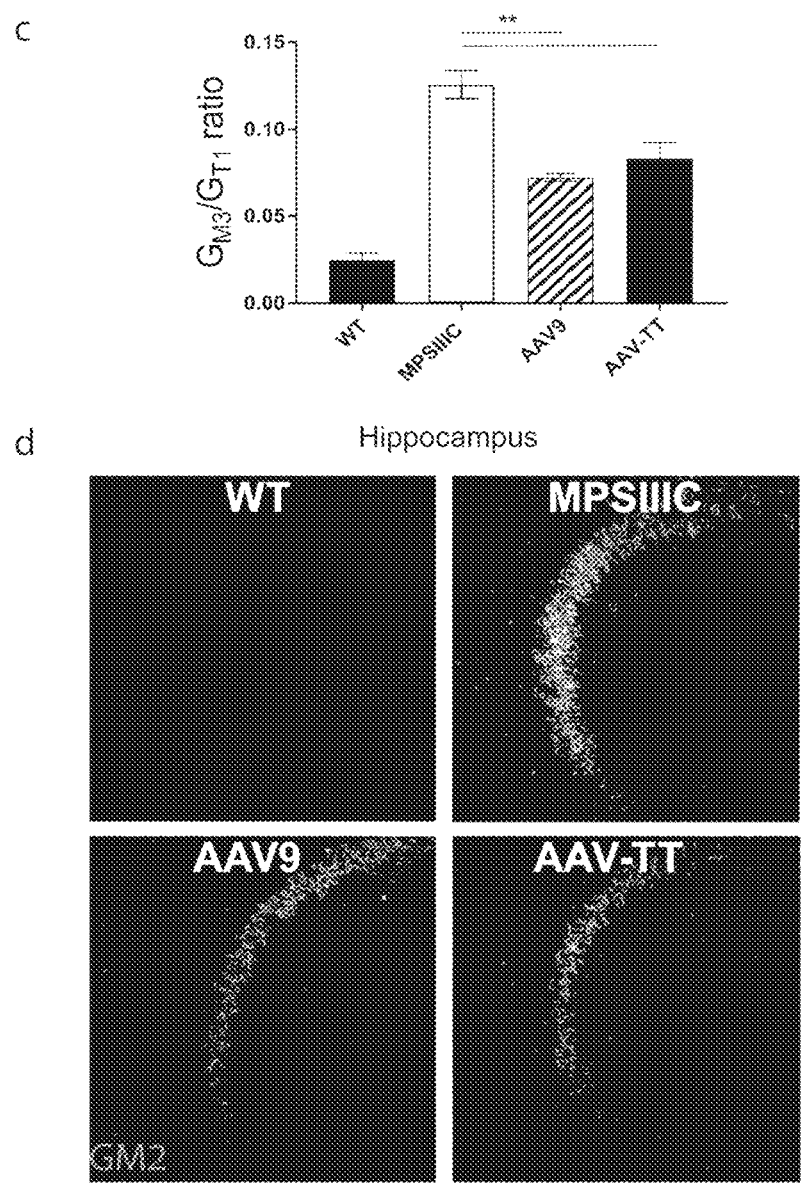
Figure 4:
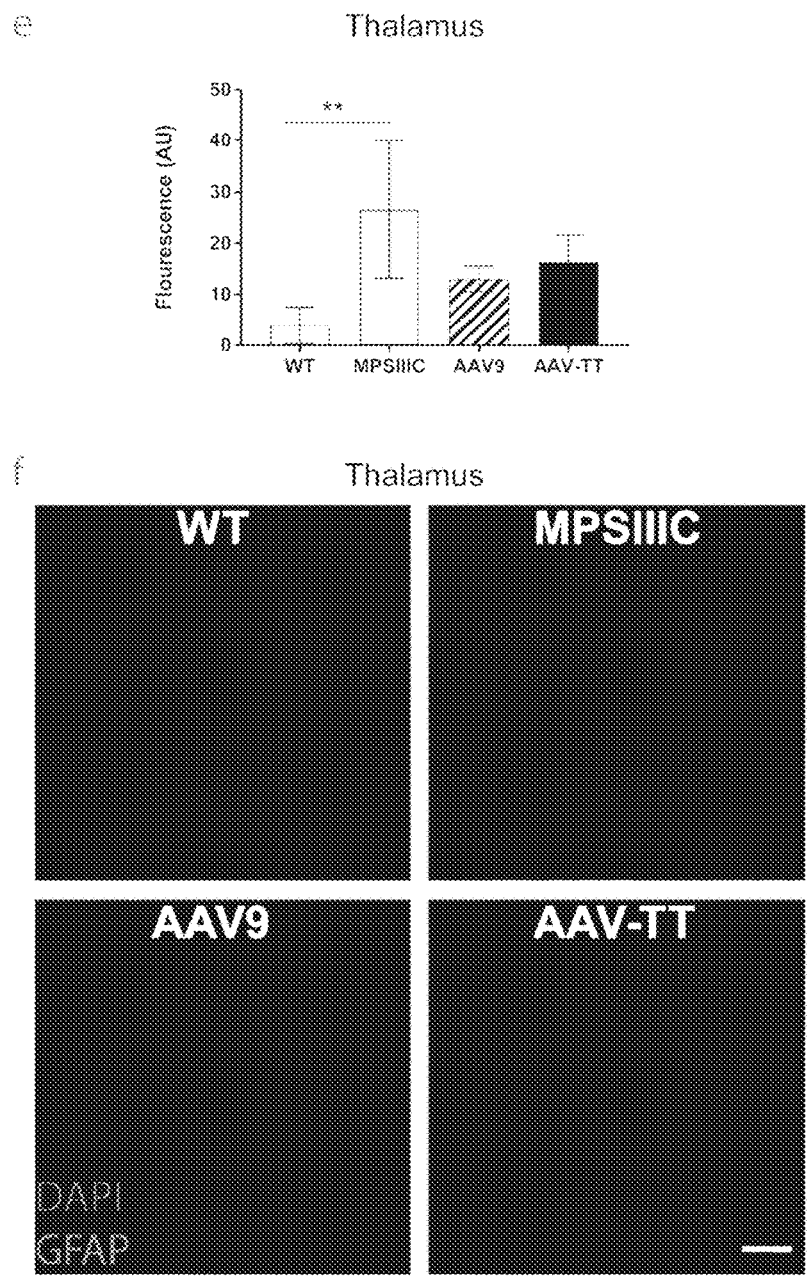
Figure 4:
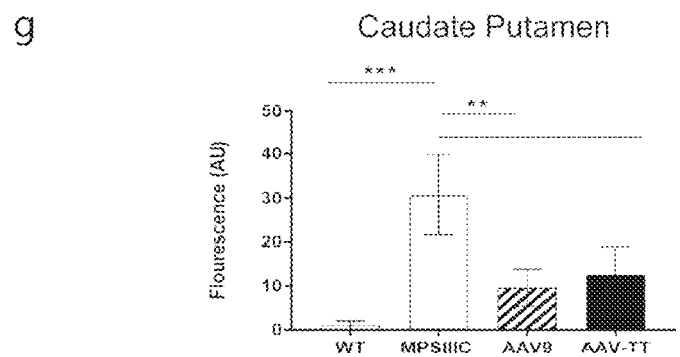
Figure 4:
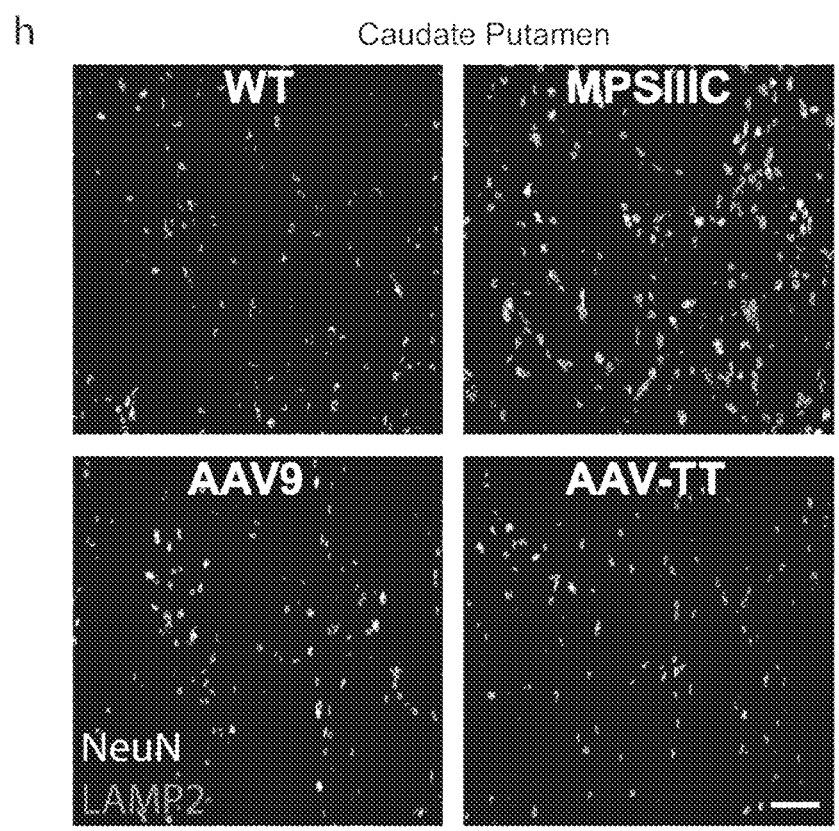
Figure 4:
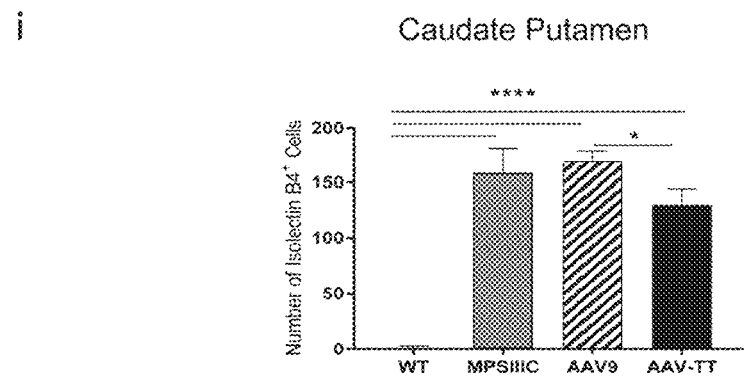
Figure 4:
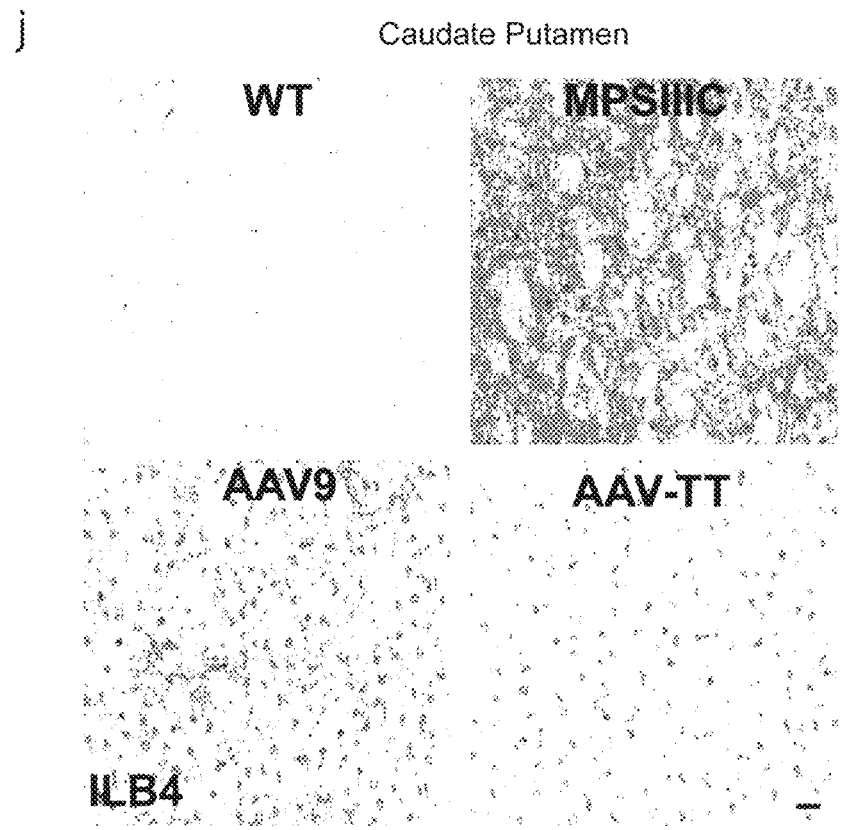
Figure 5:
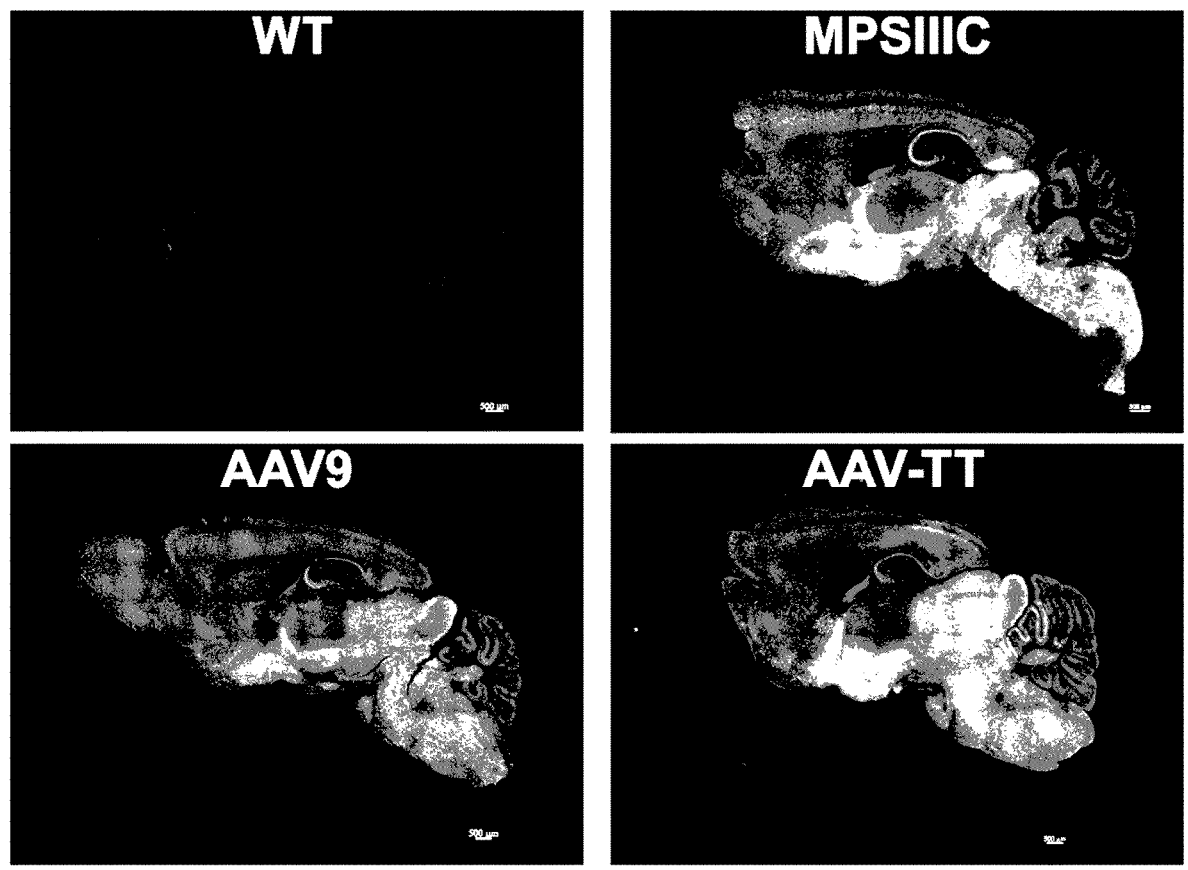
Figure 5:
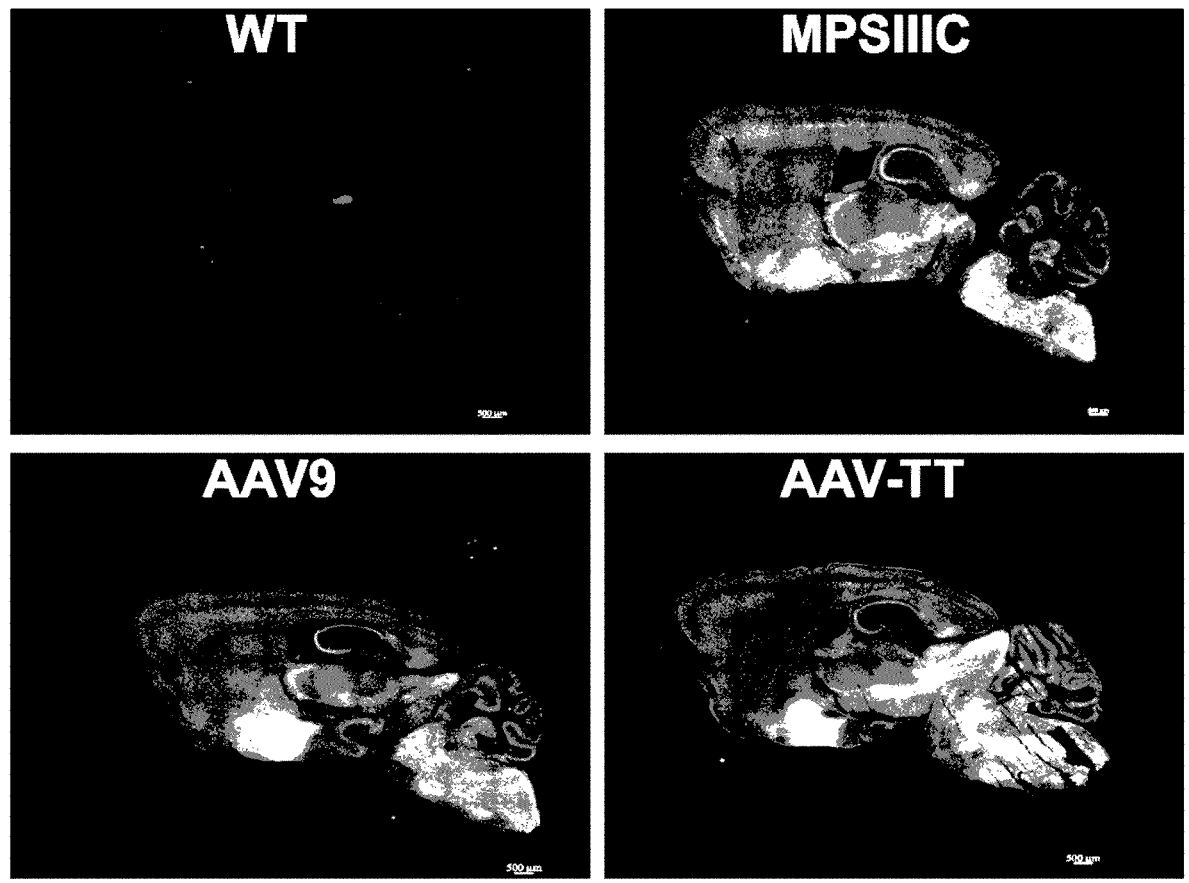
Figure 5:
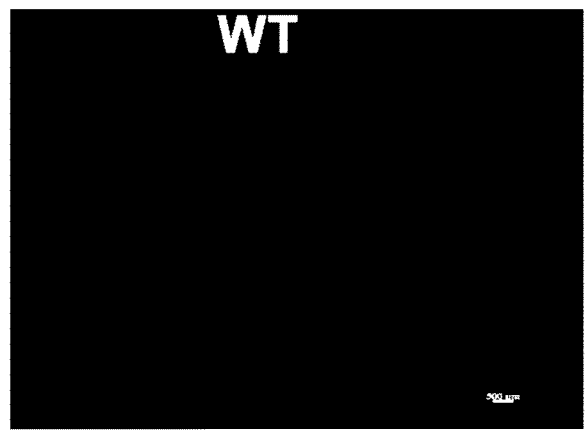
Figure 5:
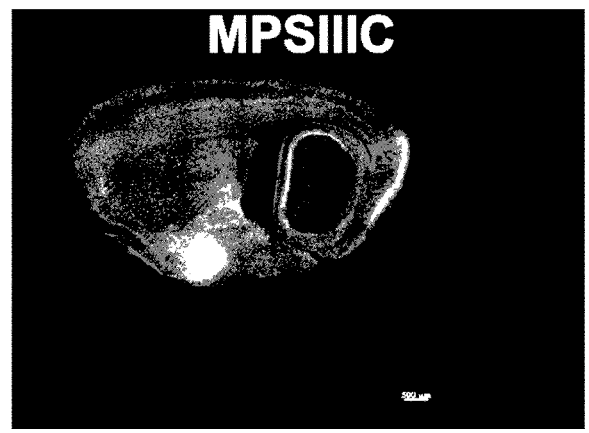
Figure 5:
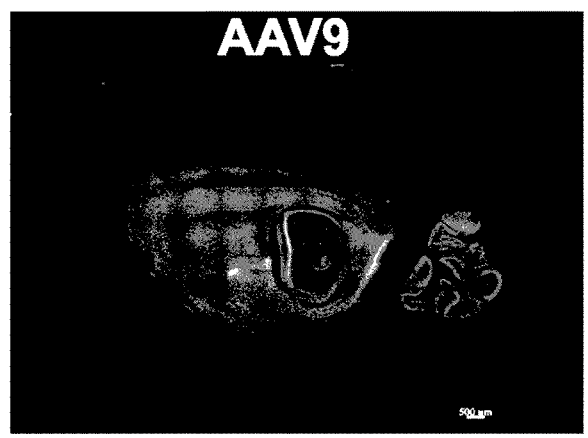
Figure 5:
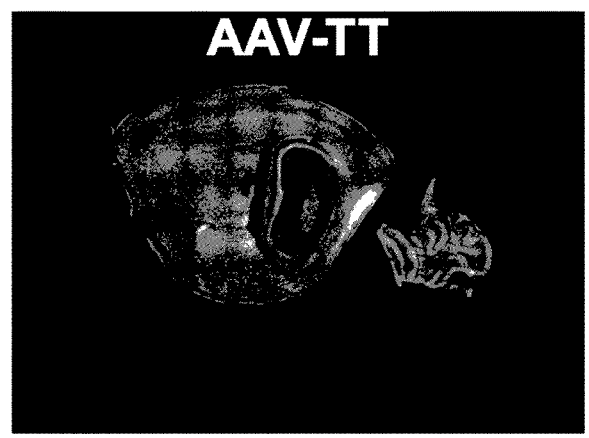
Figure 6:
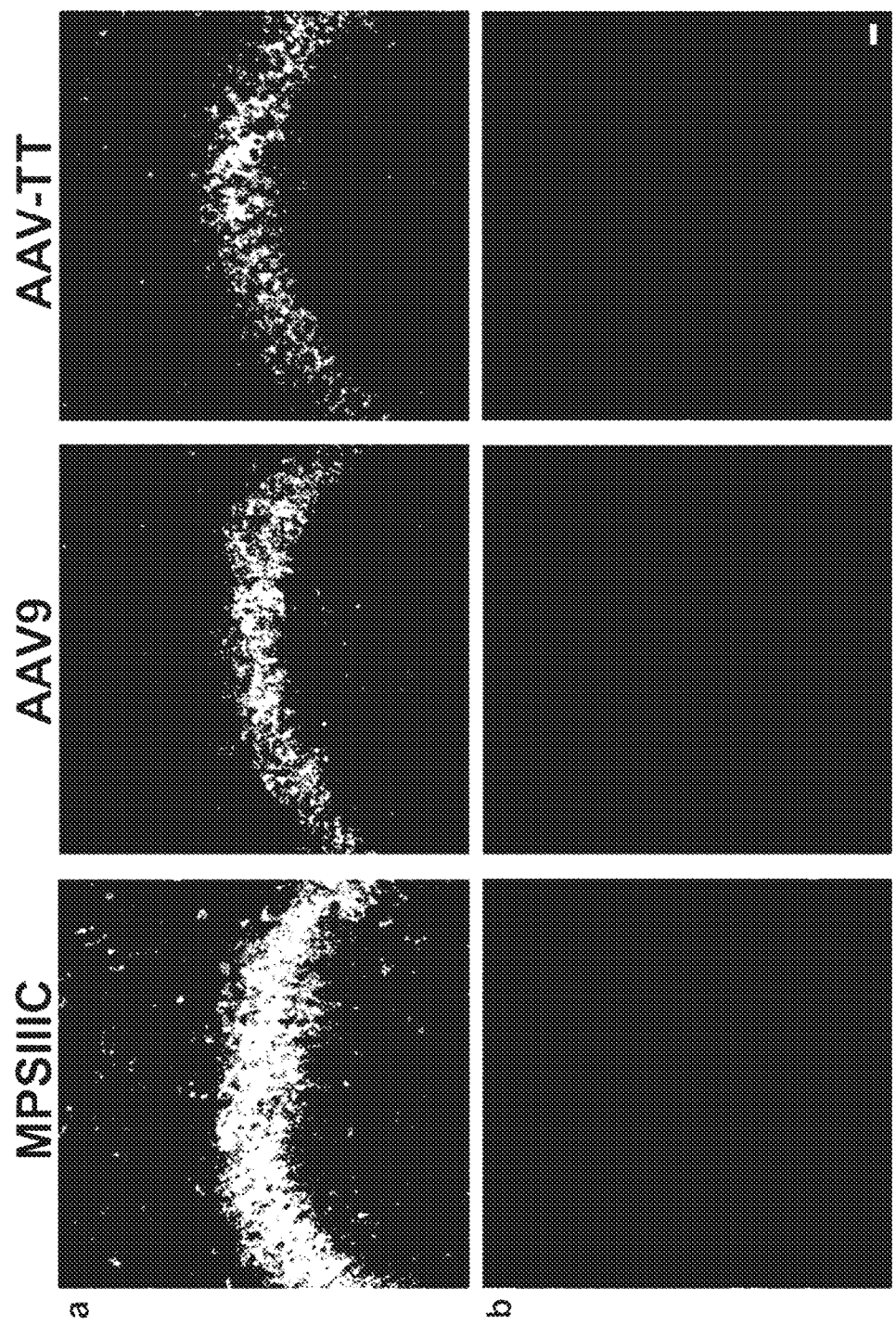
Figure 7:
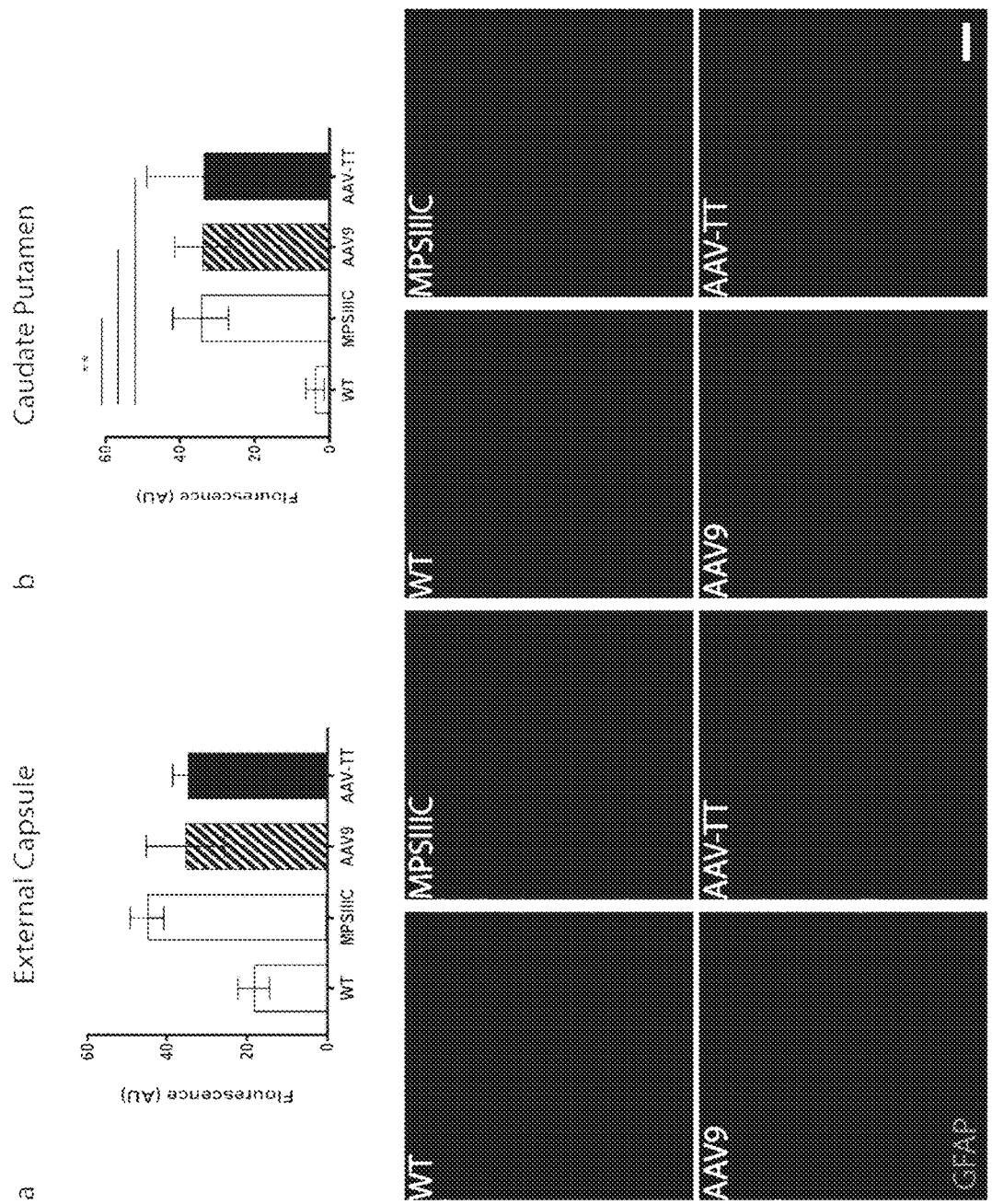
Figure 7:
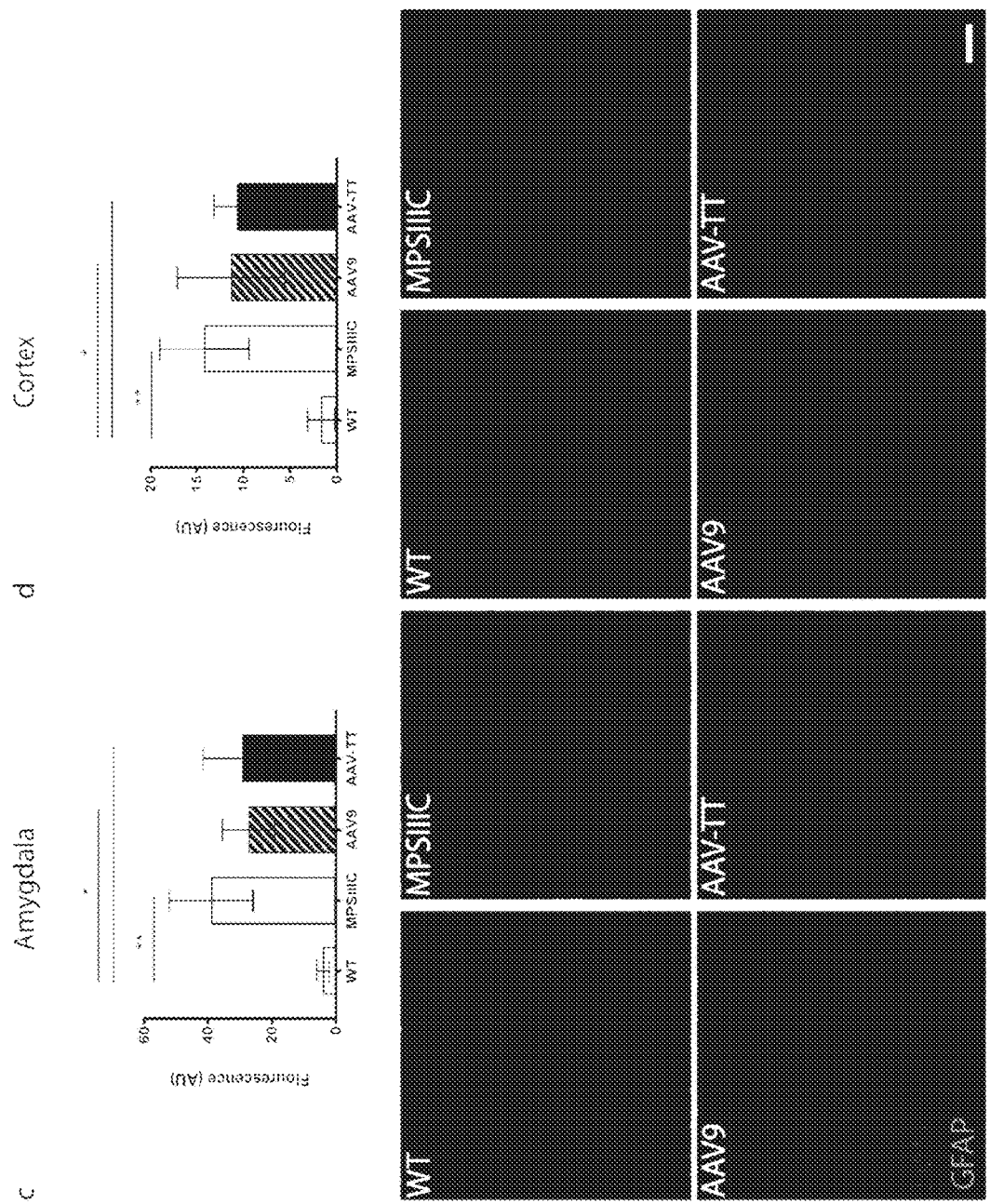
Figure 8:
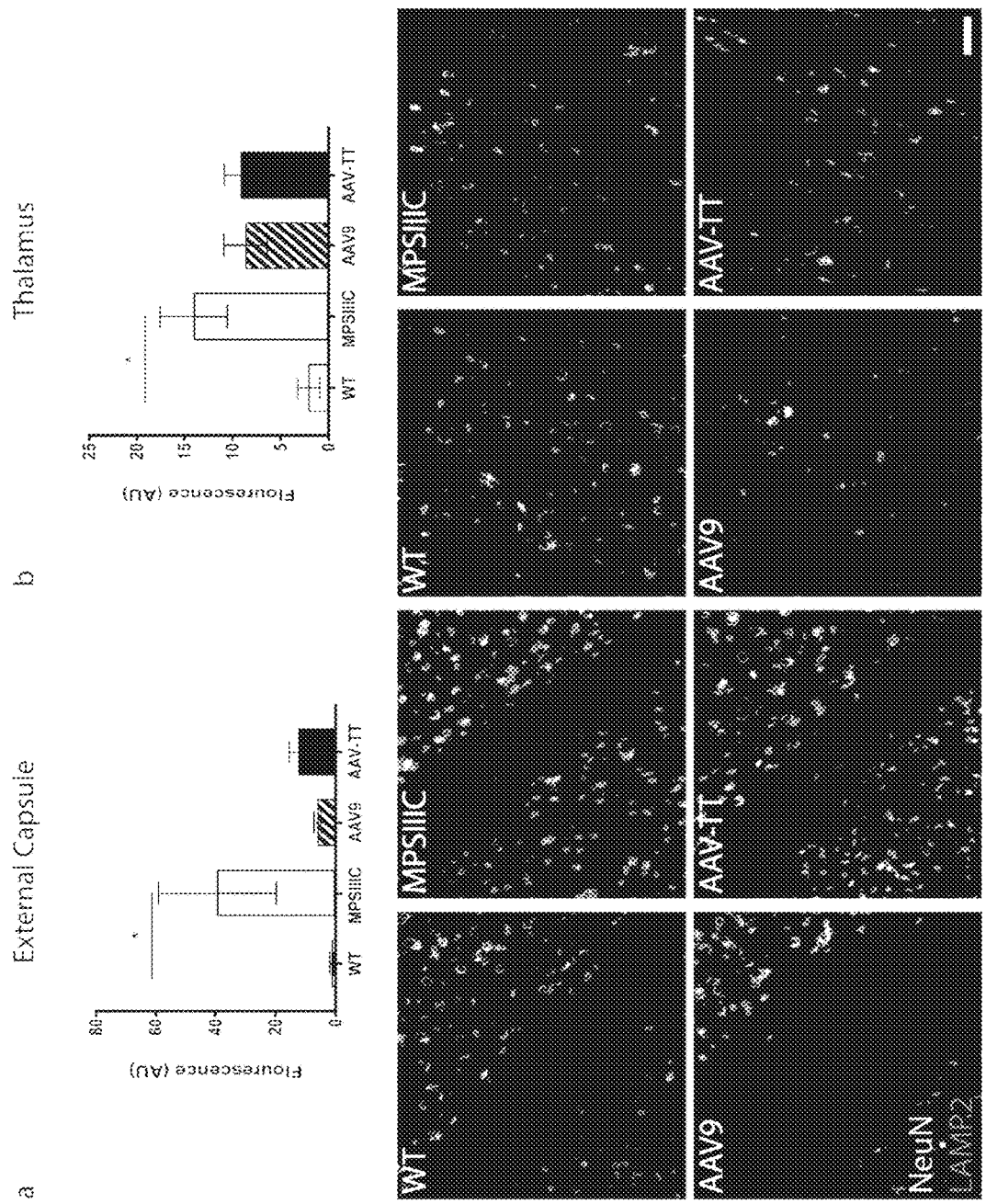
Figure 8:
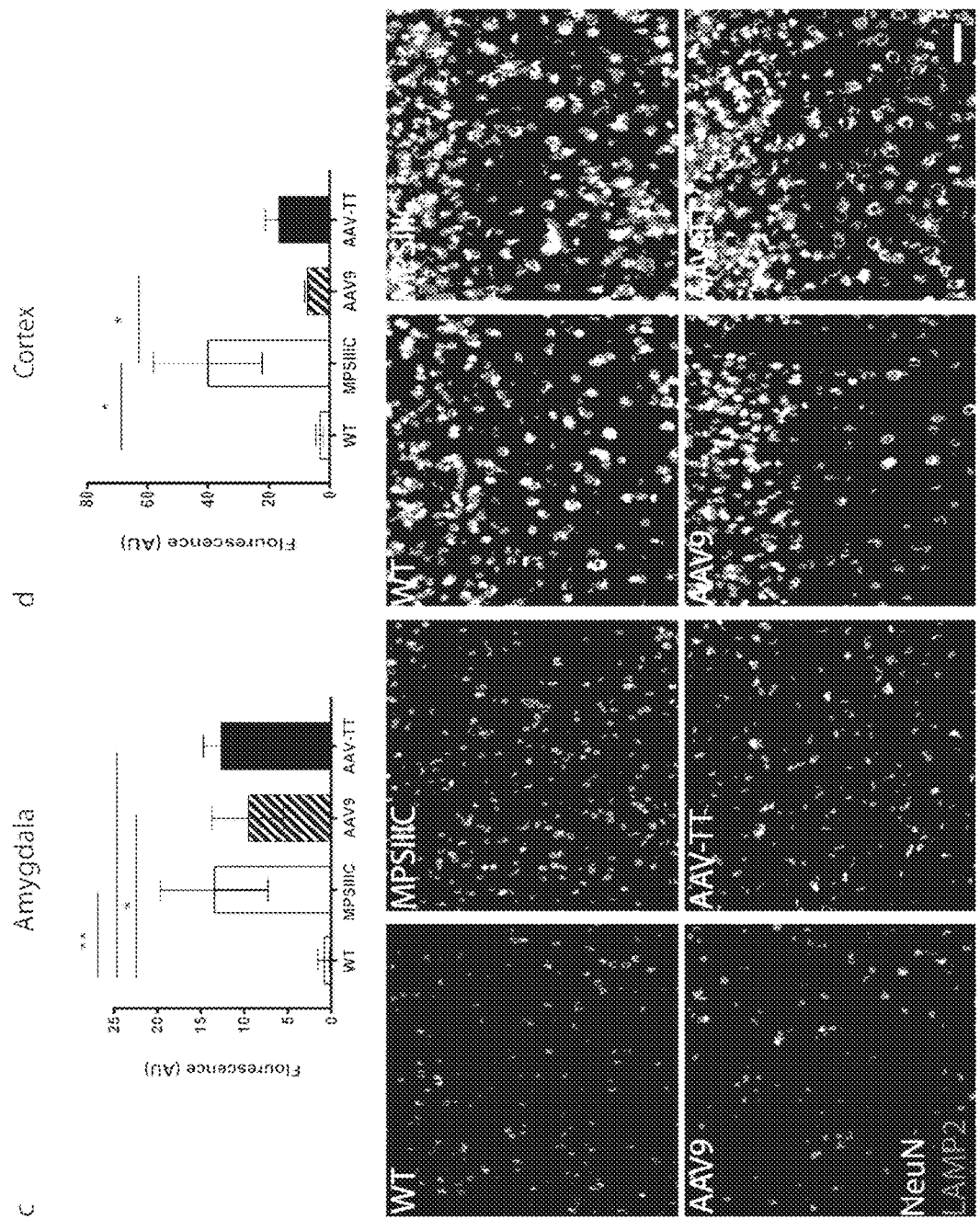
Figure 9:
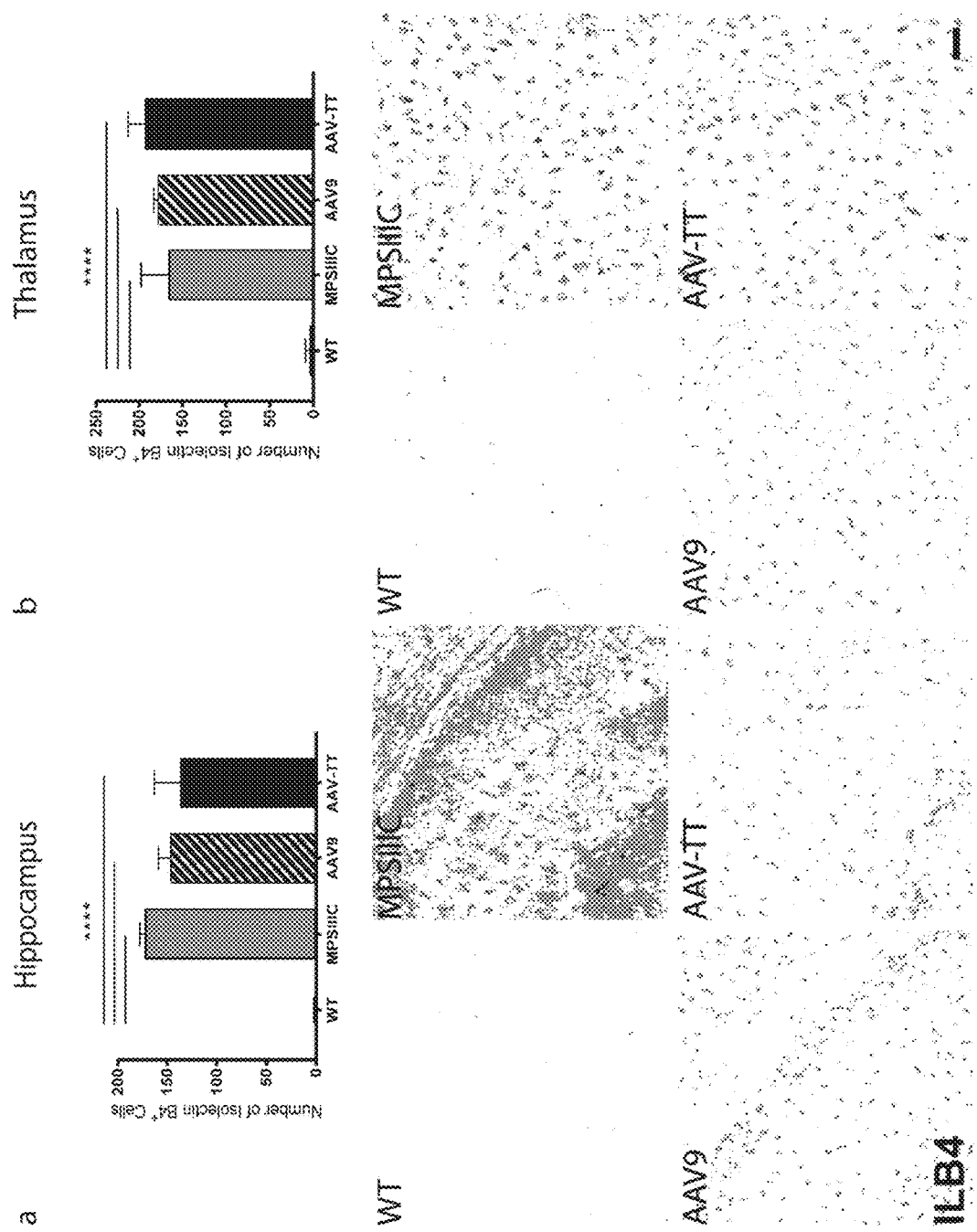
Figure 9:
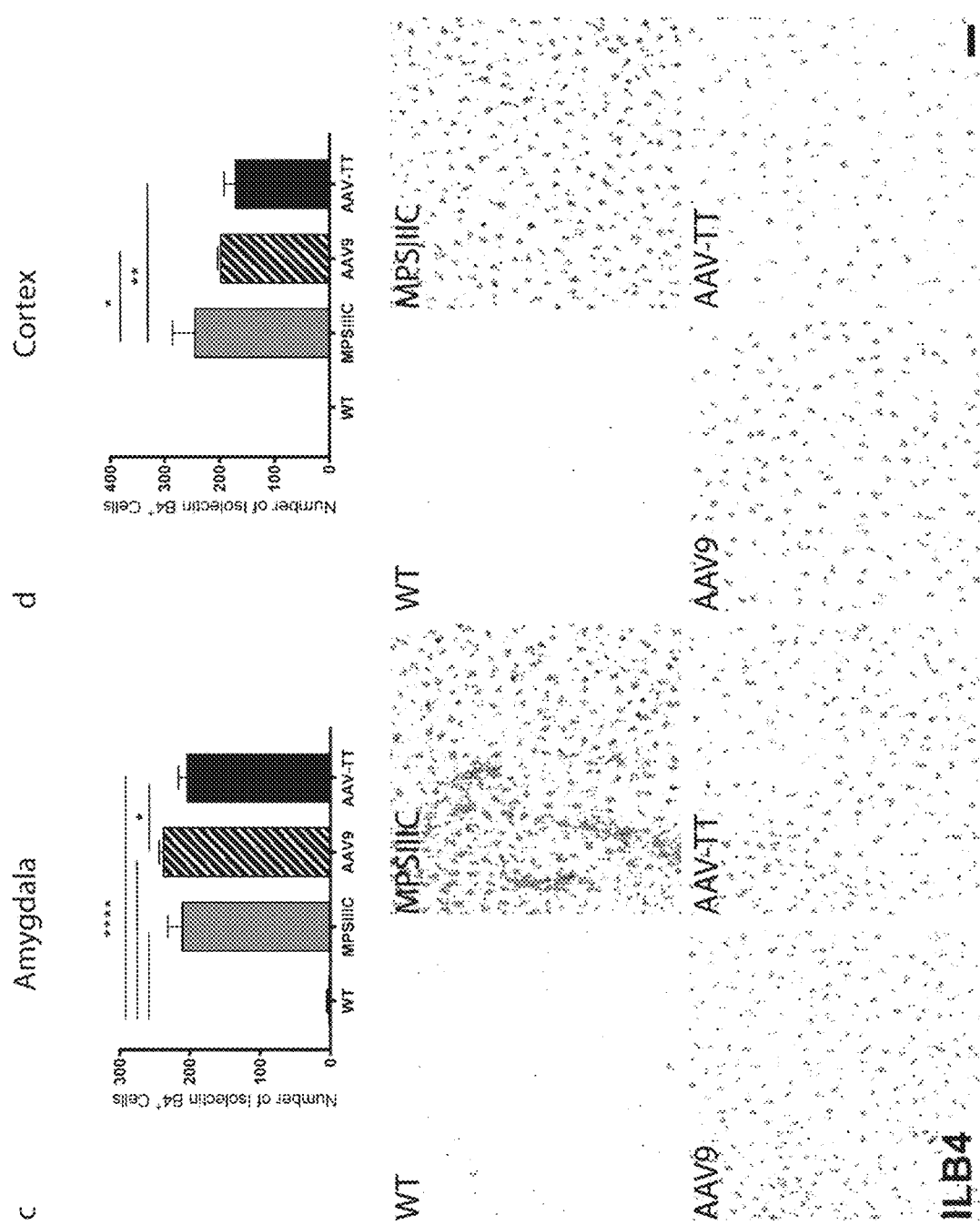

Embodiments of the present invention will now be described, by way of example only, with reference to the following experiments and accompanying figures, in which:

FIG. 1 (A) is a plasmid map for AAV-CAG-coHGSNAT and restriction digests of AAV-CAG-coHGSNAT with (B) Smal in both AAV ITRs showing that ITRs are intact and (C) Sphl and Sbfl showing the insertion of coHGSNAT into pTRUF-11;

FIG. 2 shows AAV-coHGSNAT was made using three serotypes AAV9, AAV-TT or AAV-rh10 (a) Mice received intrastriatal administration of AAV9-coHGSNAT, AAVTT-coHGSNAT or AAV-rh10-coHGSNAT and were sacrificed after 3 weeks. (b) HGSNAT is not secreted from cells. Increase in enzyme activity of AAV9-coHGSNAT, AAV-TT-coHGSNAT and AAV-rh10-coHGSNAT in brain sections R1-R5 at (c) 1 week and (d) 3 weeks post injection. Data are mean±SEM; *$p<0.05$; $p<0.01$; *$p<0.001$. (n=3-4 per group);

FIG. 3 shows (a) AAV-GFP was generated using AAV9, AAV-rh10 or AAV-TT (TT); AAV-coHGSNAT was generated using two serotypes AAV9 or AAV-TT. (b) Schematic of brain division for enzyme analysis. (c) Mice received injection of either AAV-GFP and sacrificed after 3 weeks; or AAV-HGSNAT and sacrificed after 6 months. Comparative GFP expression after 3 weeks of (d) AAV9, (e) AAV-TT or (f) AAVRh10. Bar represents 50 µm. (g) AAV-TT transduces more brain areas than AAV9 or AAVRh10. Bar represents 20 µm. (h) AAV-TT specifically transduces neurons. Improvement in (i) hyperactivity and in the Y maze, (j,k) cognitive ability in AAVTT-coHGSNAT treated mice. (l) No difference in vector copy number (vg/cell) throughout the brain. (m) Greater increase in HGSNAT enzyme activity of AAVTT-coHGSNAT than AAV9-coHGSNAT throughout the brain. (n) Increase in HGSNAT enzyme activity of AAV9-coHGSNAT and AAV-TT-coHGSNAT in brain sections R1-R5; with AAV-TT giving greater levels. No anti-AAV antibodies in (o) AAV9-coHGSNAT or (p) AAV-TT-coHGSNAT treated animals. Data are mean±SEM; *$p<0.05$; $p<0.01$; *$p<0.001$; ****$p<0.0001$. (n=7=11 for behaviour; n=6 for biochemistry);

FIG. 4 shows a reduction in (a) total HS storage by AAV9-HGSNAT and AAV-TT-coHGSNAT and (b) normalisation of the relative proportion of HS that was NAc and 2S sulfated. (c) Reduction of GM3 gangliosides in homogenised brain tissue of AAV-coHGSNAT treated mice. (d) Storage of GM3 gangliosides in the hippocampus are reduced in AAV9-coHGSNAT and AAV-TT-coHGSNAT treated mice. (e) & (f) Trend towards reduction in the accumulation of GFAP positive astrocytes in the thalamus in both AAV-coHGSNAT treated mice (g) & (h) Reduction in lysosomal LAMP2 staining in the caudate putamen in both AAV-coHGSNAT treated mice (i) & (j) Improvement in neuroinflammation in the caudate putamen seen by a reduction in number of isolection b4+ cells in AAVTT-coHGSNAT treated mice. Data are mean±SEM; *$p<0.05$; $p<0.01$; *$p<0.001$; ****$p<0.0001$. Bar represents 50 µm. (n=4-6 for HS; n=3 for GM2/GM3; n=4 for GFAP, LAMP2/NeuN, ILB4);

FIG. 5 shows representative images of GM2 ganglioside levels in WT, MPSIIIC, AAV9-coHGSNAT and AAV-TT-coHGSNAT treated mice. As the site of injection was 2 mm lateral to the bregma and 2 mm deep in the striatum the images were acquired in the sections 2.04 mm lateral from bregma (1) and two other sections equidistant to the site of injection, 1.08 mm (2) and at 3.00 mm lateral from bregma (3) using Slide Scanner Axio Scan.Z1 from Zeiss (objective 10×/0.45). Bar represents 500 µm;

FIG. 6 shows GM2 and GM3 accumulation is reduced in the specific brain areas of AAV-coHGSNAT treated MPSIIIC mice as compared to untreated mice. (a) GM3 ganglioside was significantly reduced in Medial Entorhinal cortex (MEnt) of mice treated with both AAV9-coHGSNAT and AAVTT-coHGSNAT. (b) Treatment of MPSIIIC mice with both AAV9-coHGSNAT and AAV TT-coHGSNAT vectors leads to a decrease in the accumulation of GM2 in the field CA3 of the hippocampus, as compared with untreated animals. Bar represents 20 µm;

FIG. 7 shows quantification of GFAP fluorescence and representative images of GFAP (red), DAPI (blue) staining of WT, MPSIIIC, AAV9-coHGSNAT and AAV-TT-coHGSNAT treated mice in the (a) external capsule, (b) caudate putamen, (c) amygdala and (d) cortex. Representative images are shown following staining of 4 mice per group. Bar represents 50 µm. Data are mean±SEM; *$p<0.05$; **$p<0.01$. Bar represents 50 µm;

FIG. 8 shows Quantification of LAMP2 fluorescence and representative images of LAMP2 (red)/NeuN (green) staining in WT, MPSIIIC, AAV9-coHGSNAT and AAV-TT-coHGSNAT treated mice in the (a) external capsule, (b) thalamus, (c) amygdala and (d) cortex. Representative images are shown following staining of 4 mice per group. Bar represents 50 µm. Data are mean±SEM; *$p<0.05$; **$p<0.01$. Bar represents 50 µm; and FIG. 9 shows Quantification and representative images of ILB4 (brown) staining of WT, MPSIIIC, AAV9-coHGSNAT and AAV-TT-coHGSNAT treated mice in the (a) hippocampus, (b) thalamus, (c) amygdala and (d) cortex. Representative images are shown following staining of 4 mice per group. Bar represents 50 µm Data are mean±SEM; *$p<0.05$; $p<0.01$; **$p<0.0001$. Bar represents 50 µm.

Experiments were conducted to ascertain whether an AAV vector containing an optimised HGSNAT sequence was capable of treating in a MPS IIIC mouse model whose HGSNAT gene had been disrupted.

MPS IIIC Mouse Model

An MPS IIIC mice model with targeted disruption of the HGSNAT gene was generated at the University of Montreal, Canada, as described in Martins, C., H. Hulkova, et al. (2015). "Neuroinflammation, mitochondrial defects and neurodegeneration in mucopolysaccharidosis III type C mouse model." Brain 138(Pt 2): 336-355.

AAV-HGSNAT Vector Construction

HGSNAT was codon optimised by improving the codon usage in the human HGSNAT cDNA to codons most common in human cells, removal of secondary structures and hairpins in mRNA where possible, and insertion of a Kozak sequence at the ATG start site to improve transcription. To produce the AAV-CAG-coHGSNAT vector (shown in FIG. 1), the Neo cassette was deleted and the GFP coding sequence in the pTRUF-11 plasmid was replaced by a codon-optimised HGSNAT cDNA. The codon optimised HGSNAT was inserted into the Sbfl and Sphl sites in pTRUF-11.

The cDNA for the AAV-coHGSNAT was codon optimised as follows:

| FEATURES | Location/Qualifiers |
| --- | --- |
| misc_feature | 4097 . . . 4147/label = SV$) poly A |
| rep_origin | 6652 . . . 7092/label = F1 ori |
| misc_feature | 1940 . . . 1948/label = kozac |
| misc_feature | 1949 . . . 3940/label = HGSNAT |
| polyA_site | 4161 . . . 4173/label = bGH polyA |
| misc_feature | 21 . . . 163/label = AAV2 L-ITR (pAV2) |
| misc_feature | complement 4180 . . . 4322/label = AAV2 L-ITR (pAV2)(1) /ApEinfo_label = AAV2 L-ITR (pAV2) |
| misc_feature | 19 . . . 135/label = AAV2 R-ITR (pAV2) |
| misc_feature | complement(4208 . . . 4324)/label = AAV2 R-ITR (pAV2)(1) |
| misc_feature | 4180 . . . 4324/label = ITR |
| misc_feature | complement(19 . . . 163)/label = ITR(1) |
| misc_feature | 168 . . . 520/label = CMV/IE/enhancer |
| misc_feature | 413 . . . 825/label = Chicken\beta-actin\promoter |
| misc_feature | 826 . . . 919/label = Chicken beta-actin exon |
| misc_feature | 920 . . . 1027/label = Chicken beta-actin intron |
| misc_feature | 1804 . . . 1844/label = Rabbit beta-globin intron |
| misc_feature | 1845 . . . 1898/label = Rabbit beta-globin exon 2 |
| misc_feature | 1028 . . . 1803/label = CBAP promoter |
| rep_origin | complement(4568 . . . 5250)/label = ColE1 origin |
| rep_origin | complement(6774 . . . 7080)/label = F1 ori(1) |
| rep_origin | complement(6642 . . . 7097)/label = M13 origin |
| CDS | complement(5348 . . . 6007)/label = AmpR |

AAV Production and Titration

AAV was produced using transient transfection of HEK 293T cells from a by polyethylenimine (PEI) with three GLP plasmids: cis ITR transgene (AAV-CAG-coHGSNAT), rep (AAV2 sequence)/cap helper plasmid either True-Type (TT) or AAV9 and HGTI adenoviral helper plasmid. Cells were harvested 72 hours post transfection allowing for maximum virus production. A recombinant virus is retained within the cells and the crude cell lysate is produced by a three freeze thaw cycles to release the virus. The virus from the supernatant was precipitated with ammonium sulphate salt; cell lysate and supernatant were further treated with benzonase to digest cellular and non-encapsidated DNA.

AAVTT-coHGSNAT and AAVRh10-coHGSNAT was purified by AVB sepharose column and AAV9-coHGSNAT by iodixanol step gradient. All viruses were titred via qPCR.

Intracranial Injections

Prior to surgery, mice were anesthetized with 4% isoflurane in 4 L/min $O_2$ for induction, and maintained by 2% isoflurane in 2 L/min $O_2$. The cranium was fixed to a stereotaxic surgical rig by inserting ear bars into the external auditory meatus and by securing the incisors into the incisor adaptor. A midline incision was made and the skin retracted to expose the cranial vault and expose the bregma and lambda. The stereotactic coordinates used are based on the mouse brain atlas (Franklin and Paxinos), and the target area is within each striatum. The striatum is located 2 mm lateral, and 3 mm deep to the bregma. The entry point was recorded and a burr-hole drilled using a handheld electric drill until the inner table is breached.

All mice received bilateral injections of $5.2 \times 10^9$ viral genomes of either AAV9-coHGSNAT or AAVTT-coHGSNAT ($2.6 \times 10^9$ viral genomes/hemisphere) in a total volume of 6 μL (3 μL/hemisphere). AAV9-coHGSNAT and AAVTT-coHGSNAT ($2.6 \times 10^9$ viral genomes) was delivered into the striatum with a 5 μl, 26-gauge Hamilton syringe at a rate of 0.5 μL/min (3 μL/hemisphere). Sham mice received either phosphate-buffered saline (PBS) or AAV-GFP (3 μL/hemisphere). The needle was left in place for an additional 5 min after each infusion to ensure complete delivery of the virus. The skin incision was then closed with a 6/0 vicryl suture Mice were monitored for two weeks post injection and were checked for post-operative complications such as wound breakdown and infection.

Sample Processing

Mice were anesthetized and transcardially perfused with 37° C. PBS to remove blood from organs. Pieces of liver and spleen and one hemisphere of brain were frozen at −80° C. The other brain hemisphere was fixed in 4% paraformaldehyde for 24 hours, then 30% sucrose 2 mmol/L $MgCl_2$/PBS for 48 hours before freezing at −80° C. For HGSNAT and HS assays, samples were homogenized and sonicated in homogenization buffer (0.5 mol/L NaCl, 0.02 mol/l Tris pH 7-7.5), then centrifuged at 2,200 g for 15 minutes at 4° C., and the supernatant was collected. Protein concentration was determined using Pierce BCA assay kit (Fisher Scientific, Loughborough, UK) assay according to manufacturer's instructions.

HGSNAT Enzyme Assay

HGSNAT activity was measured using the HGSNAT activity assay using 4-methylumbelliferyl-β-D-N-glucosaminide (MU-βGlcNH2, Moscerdam, The Netherlands) according to manufacturer's instructions in hemicoronal fifths. The injection site was in section R2 (rostral to caudal) close to the border of R2/R3. HGSNAT enzyme activity was measured in sections R1-5 of each mouse brain. Brain homogenates (60 μg of total protein) were incubated with 10 μL acetyl co-enzyme and 10 μL substrate for 18 hours at 37° C. and the reaction terminated with 200 μL carbonate buffer pH 9.5. HGSNAT activity was calculated using a standard curve as the amount (μM) 4-MU generated/mg protein/18 hours.

Analysis of Glycosaminoglycans in Mouse Tissues.

Total GAG were extracted from brain and liver tissues as described in Wilkinson, et. al. (2012) Neuropathology in mouse models of mucopolysaccharidosis type I, IIIA and IIIB. PLoS One. 2012; 7(4):e35787. Briefly, tissues were pronase treated before GAGs were purified using a DEAE-sephacel column. Following desalting HS chains were digested into their component disaccharides using a combination of bacterial heparinases I, II and III enzymes. Resultant disaccharides were labelled with 2-aminoacridone (AMAC) and separated by RP-HPLC. Duplicate heparinise digestions followed by RP-HPLC were performed per brain. Integration analysis of disaccharide peak-areas enabled relative quantification of HS amounts and disaccharide composition to be calculated. The percentage of total disaccharides containing either an N-acetylated or N-sulphated glucosamine, or containing 6-Osulphation of GlcNAc or GlcNS or 2-O-sulphation of IduA or GlcA was also calculated from disaccharide compositions analyses, by summing the total number of disaccharides with that modification.

Open-Field Behaviour

Each mouse was tested at 6 months of age 1.5 hours into the 12-hour light phase to ensure the same circadian time point. Mice were dropped into the centre of an open-field arena (width 450 mm, depth 450 mm, height 500 mm) made of matt white acrylic; and behaviour was recorded for 1 hour using a digital camcorder. The data were analysed using TopScan suite software version 2.0 (Clever Sys, Reston, Va.).

Spontaneous Alternation

Spontaneous alternation was assessed during one continuous 10 min session in a Y-maze consisting of three identical arms. The test mouse was placed in the centre of the maze and allowed to move freely in the arm. Spontaneous alternation was described as successive entries into three arms, in overlapping triplet sets. The effect was calculated as percent alternation=[(no of alternations/total number of arm entries)−2]×100 (chance level=33%).

Indirect Enzyme-Linked Immunosorbent Assay (ELISA) Detection of Anti-AAV Antibodies Briefly, micropipette plates were coated with $2\times10^9$ vg/ml of each virus in 50 uL/well coating buffer (0.1M $NaHCO_3$, pH 8.5) and incubated overnight at 4 C, and blocked with (1% BSA, 0.02M Tris/HCl, 025M NaCl, pH 7.0). Eight 2-fold serial dilutions were prepared with dilution buffer (PBS, 0.05% Tween, 0.01% BSA) for each brain sample with a starting protein concentration of 10 μg. 50 μl of each brain serial dilution were applied to the plate in duplicate and incubated for 1 hour at room temperature, then aspirated and washed 3 times with wash buffer. 100 μl of 5 μg/ml biotinylated goat anti-mouse IgG antibody in dilution buffer was added to each well and incubated at room temperature for 1 hour, aspirated and washed 3 times with wash buffer. Each well was incubated with 100 μl of Vectastain ABC kit prepared according to the manufacturer instruction for 30 minutes at room temperature; this was then aspirated and washed as previously described. 100 μl of TMB substrate was loaded to each well and incubated for exactly 5 minutes at room temperature. The reaction was stopped by adding 50 μl of 2.5M $H_2SO_4$ to each well. Light absorbance was read at 450 nm to determine the maximum absorbance and at 570 nm to correct for measurement errors on a Synergy HT microplate spectrophotometer (Biotek) with Gen 5 software.

Vector Copy Number

Analysis of vector biodistribution was performed by quantitative PCR (qPCR). Genomic DNA from tissue homogenate was extracted using Qiagen DNeasy Blood and Tissue Kit. For quantification of AAV vector copy numbers, a standard curve was prepared by adding specific amounts of linearized AAV-HGSNAT plasmid and compared against GAPDH using naïve genomic murine DNA. Plasmid amounts were calculated to give the numbers of double-stranded vector genomes per diploid genomic equivalent.

Analysis of Brain Gangliosides by TLC

Frozen brain tissues were homogenized in water (10% v/w) using a FastPrep-24 MP homogenizer. Lipids were extracted by addition of 2 volumes of methanol and 1 volume of chloroform to one volume of the homogenate. After 10 min centrifugation at 1000 g the organic phase was collected, and used to analyse gangliosides by phase separation. The upper phase containing gangliosides was isolated and passed through a Supelclean LC-18 column (Supelco). Gangliosides were eluted first using methanol and then the chloroform/methanol mixture. After evaporation under a stream of nitrogen, the residue was re-suspended in 0.1 ml of the chloroform/methanol mixture and applied to a silica gel thin-layer chromatography (TLC) plate that was developed using chloroform/methanol/0.22% $CaCl_2$ (55:45:10, by volume). After staining with orcinol, gangliosides were identified by comparing their Rf to those of authentic porcine brain ganglioside standards (Avanti Polar Lipids). Lipids present in the lower phase were separated by TLC using chloroform/methanol/ammonia/water (70:30:2:3, by volume).

Immunofluorescence of GFP/NeuN/GFAP/LAMP2

Sections (30 μm) were blocked in 5% goat serum, 1% Triton-X-100 in TBS for one hour at room temperature, incubated overnight at 4° C. with primary antibodies made up in blocking solution, washed in PBS, and incubated in secondary antibody diluted in blocking solution for one hour. The primary antibodies used for the co-labelling experiments in this study were as follows: chicken anti-GFP (1:1000), rabbit anti-NeuN (1:500), rabbit anti-GFAP (1:1500), rat anti-LAMP2 (1:200) Secondary antibodies used were AlexaFluor 488 goat anti-chicken (1:1000), AlexaFluor 488 goat anti-rabbit (1:1000), AlexaFluor 488 goat anti-rat (1:1000), AlexaFluor 594 goat anti-rat (1:1000), AlexaFluor 594 goat anti-rabbit (1:1000), Sections were mounted using ProLong Gold Antifade medium (Life Technologies)

Immunofluorescence of GM2 Gangliosides

Sagittal sections (40 μm) were treated with 1% Triton X-100, blocked with 10% goat serum in PBS and incubated overnight at 4° C. with primary mouse humanized anti-GM2 (KM966, 1:400) antibodies in 3% goat serum, 0.1% Triton X-100 in PBS. The slides were further stained with DyLight 488-conjugated Affinipure Goat anti-human IgG antibodies (Jackson Immunoresearch laboratories). The slides were mounted with Vectashield mounting medium.

Isolectin B4 (ILB4) Staining

Coronal sections (30 μm) were stained using peroxidase-conjugated isolectin B4 (ILB4) from *Bandeiraea simplicifolia* (*Griffonia simplicifolia*) (ILB4, L5391, Sigma). Briefly, sections were blocked in 1% $H_2O_2$ in TBS for 30 minutes at room temperature, and incubated overnight at 4° C. with ILB4 diluted to 5 μg/ml in TBS/$Mg^{2+}$/$Ca^{2+}$ buffer. Staining was visualised using Vectastain avidin-biotin solution (ABC, Vector Labs) and DAB (Sigma), after which the sections were mounted, dehydrated and coverslipped with DPX (Sigma).

Results

A novel AAV serotype (AAV-TT) was engineered to include key residues found in natural variants of AAV2, resulting in a gene therapy vector with extraordinary transduction characteristics in the CNS. GFP expression of AAV9, Rh10 and AAV-TT were compared in the brains of mice, demonstrating improved distribution of AAV-TT-GFP in the brain over AAV9-GFP and AAV-Rh10-GFP. AAV-TT-GFP specifically transduces neurons in the adult mouse brain. The therapeutic efficacy of AAV expressing the codon optimised HGSNAT transgene (coHGSNAT) using the two best serotypes AAV9-coHGSNAT and AAV-TT-coHGSNAT were compared in a long-term study in MPSIIIC mice, delivered via bilateral intracranial injections.

Short term enzyme activity was assessed at 1 and 3 weeks post injection (FIG. 2a), in hemicoronal fifths. It was confirmed that HGSNAT is a non-secreted enzyme. Relative HGSNAT activity was assessed in vitro by transiently transfecting HEK293T cells with a plasmid containing coHGSNAT. After 72 hours, intracellular enzyme activity of the HGSNAT transfected cells was significantly higher than GFP transfected cells (FIG. 2b). However, HGSNAT activity could not be detected in the supernatant. Enzyme activity in the brain was significantly elevated above WT in all treated groups; however, this treatment was localised around the injection site (as shown in FIG. 2c 1 week and 2d 3 weeks post injection). At this early stage, the AAV9 serotype had higher enzyme levels than AAV-TT and AAVRh10. In preparation for pre-clinical studies in a mouse model of MPSIIIC, we quantified the efficiency of gene transfer of AAV-TT against AAV serotypes currently used in the brain (FIG. 3a-c). Intracerebral injection of AAVTT-GFP was compared to AAV9-GFP and AAVRh10-GFP, both of which are commonly used for neurological applications. For each serotype, equivalent viral titres were injected bilaterally into adult mouse brains ($2.6 \times 10^9$ vg/hemisphere) and GFP expression was assessed after 3 weeks (FIG. 3 d-f). GFP intensity and distribution varied significantly among serotypes. AAV-TT resulted in greater global transduction of cells throughout the brain compared to both AAV9 and AAVRh10; in which spread of vector was limited (FIGS. 3 d-f). AAV9 gave intense staining in the areas close to the injection site, especially around the needle track (FIG. 3g) with limited or no distribution in other areas. In contrast, GFP expression of AAV-TT was less intense than AAV9 and AAVRh10 but more widely distributed in the brain resulting in a greater number of areas transduced; including areas of both white and gray matter. The main areas transduced by AAV-TT were the cingulate cortex, external capsule, thalamus, amygdala, somatosensory cortex and the hippocampus respectively (FIG. 3g). Both AAV9 and AAV-TT resulted in greater transduction areas than AAVRh10. AAV-TT transduced of both the soma and the axon of neurons, positive neuronal staining was confirmed by co-localization of GFP with NeuN+ neuronal nuclei (FIG. 3h).

Our data demonstrate improved distribution of AAV-TT in the brain over AAV9 and AAVRh10, therefore we subsequently compared the therapeutic efficacy of AAV vectors expressing the codon optimised human HGSNAT (coHGSNAT) transgene using the two best serotypes AAV9 and AAV-TT. Four months after bilateral intracranial injections ($2.6 \times 10^9$ vg/hemisphere) of these vectors into MPSIIIC mice, we measured behavioural outcomes; biochemical and histological outcomes were measured 6 months post-treatment (FIGS. 3 i-p). At 4 months post injection, behaviour was corrected in AAV-TT-HGSNAT treated MPSIIIC mice over AAV9-coHGSNAT. Hyperactivity (FIG. 3i) and in the Y maze (FIG. 3k) cognition (FIG. 3j) were improved in AAVTT-coHGSNAT treated MPSIIIC mice compared to Sham treated MPSIIIC mice.

Interestingly, no statistically significant differences was found in vector copy numbers in the brain among the groups with average numbers of $39.15 \pm 16.91$ and $45.09 \pm 16.29$ (FIG. 3l).

At 6 months post treatment, intracranial injection of AAV-TT and AAV9 vectors expressing coHGSNAT increased enzyme activity levels to above WT levels; higher levels were obtained in AAV-TT treated mice compared to AAV9-treated mice (FIG. 3m). This effect was localised around the injection site as the brain was dissected into five coronal slices (anterior to posterior R1-R5; 3n); injections of AAV-TT resulted in higher levels of enzyme activity in sections R2 than AAV9.

As illustrated by FIG. 3, no anti-AAV IgG antibodies were detected in the brains of AAV-coHGSNAT treated mice using serotype (FIG. 3o) AAV-9 and (FIG. 3p) AAV-TT 6 months after injection. Positive controls for each serotype were generated by subcutaneous co-injection of adjuvant and AAV serotype in WT mice.

To determine if the primary storage substrate heparan sulphate (HS) could be reduced by the treatment, the total amount of HS was determined by 2-aminoacridone (AMAC)-labelled disaccharide analysis. MPSIIIC mice display approximately a 14.7-fold increase in brain HS levels compared to WT (FIG. 4a). Overall, AAV9-coHGSNAT and AAV-TT-coHGSNAT reduced total HS levels. The reduction in HS levels was greater in AAV-TT-coHGSNAT treated mice, with no significant differences observed compared to WT mice (FIG. 4a).

Significant increases in the amounts of highly sulphated UA2S-GlcNS(6S) and UA(2S)-GlcNS HS species were seen in the brains of MPSIIIC mice; with a reduction in the unsulphated UA-GlcNAc groups. There were no significant differences between WT and MPSIIIC mice in the proportion of UA-GlcNS(6S), UA-GlcNS and UA-GlcNAc(6S) HS disaccharides. Treatment with AAV-TT-coHGSNAT corrected UA(2S)-GlcNS and UA-GlcNAc, whereas AAV9-coHGSNAT did not (FIG. 4b).

It has been previously reported that both GM3 and GM2 gangliosides are significantly increased in the brains of MPSIIIC mice. AAV-coHGSNAT treatment with both serotypes significantly reduced the levels of GM3 gangliosides in the brains of MPSIIIC mice at 6 months post injection (FIG. 4c). Both serotypes were equally effective for reduction of GM3, which was decreased ~2-fold (FIG. 4c). GM2 ganglioside levels were reduced in the hippocampus in both groups of treated mice compared to untreated mice (Figure. 4d). GM2 ganglioside was observed in most areas of the brain, but was more prominent in the amygdala, pons, medulla, midbrain, hypothalamus, reticular nucleus of the thalamus, medial entorhinal cortex, cortex, hippocampus and cerebellum. The levels of GM2 ganglioside showed a trend for reduction in response to the AAV treatment (FIG. 5). Quantification of confocal images showed that GM3 ganglioside (FIG. 6a) and GM2 ganglioside (FIG. 6b) was significantly reduced in Medial Entorhinal cortex (MEnt) area of mice treated with both AAV9 and AAV-TT vectors.

Astrocytosis was observed in the thalamus of MPSIIIC with nonsignificant reductions of GFAP (FIGS. 4e & f), external capsule (FIG. 7a), near the injection site in the caudate putamen; with no differences in GFAP positive astrocytes between MPSIIIC and both treated groups (FIG. 7b). amygdala (FIG. 7c) and the cortex (FIG. 7d). Levels of LAMP2 lysosomal storage were significantly decreased by both vectors in the caudate putamen (FIG. 4g & h), an area close to the injection site. A similar trend was seen in areas away from the injection site including the external capsule (FIG. 8a), thalamus (FIG. 8b), amygdala (FIG. 8c), and cortex (FIG. 8d). Immunohistochemical analysis of the brain showed a greater reduction of inflammation in terms of the number of isolectin B4 positive cells in AAV-TT-coHGSNAT than AAV9-coHGSNAT treated mice in the caudate putamen (FIGS. 4i & j), the amygdala (FIG. 9c), and the cortex (FIG. 9d), no differences were observed in the hippocampus (FIG. 9a) and the thalamus (FIG. 9b).

The forgoing embodiments are not intended to limit the scope of the protection afforded by the claims, but rather to describe examples of how the invention may be put into practice.

| | Sequence Listings |

SEQ ID No. 1
```
gggggggggg ggggggggtt ggccactccc tctctgcgcg ctcgctcgct cactgaggcc    60
gggcgaccaa aggtcgcccg acgcccgggc tttgcccggg cggcctcagt gagcgagcga   120
gcgcgcagag agggagtggc caactccatc actagggtt cctagatctg aattcggtac   180
cctagttatt aatagtaatc aattacgggg tcattagttc atagcccata tatggagttc   240
cgcgttacat aacttacggt aaatggcccg cctggctgac cgcccaacga cccccgccca   300
ttgacgtcaa taatgacgta tgttcccata gtaacgccaa tagggacttt ccattgacgt   360
caatgggtgg actatttacg gtaaactgcc cacttggcag tacatcaagt gtatcatatg   420
ccaagtacgc cccctattga cgtcaatgac ggtaaatggc ccgcctggca ttatgcccag   480
tacatgacct tatgggactt tcctacttgg cagtacatct acgtattagt catcgctatt   540
accatggtcg aggtgagccc cacgttctgc ttcactctcc ccatctcccc ccctcccca   600
cccccaattt tgtatttatt tatttttaa ttattttgtg cagcgatggg gcggggggg   660
ggggggggggc gcgcgccagg cggggcgggg cggggcgagg ggcggggcgg ggcgaggcgg   720
agaggtgcgg cggcagccaa tcagagcggc gcgctccgaa agtttccttt tatggcgagg   780
cggcggcggc ggcggcccta taaaagcga agcgcgcggc gggcgggagt cgctgcgacg   840
ctgccttcgc cccgtgcccc gctccgccgc cgcctcgcgc cgcccgcccc ggctctgact   900
gaccgcgtta ctcccacagg tgagcggcgc ggacgccct tctcctccgg gctgtaatta   960
gcgcttggtt taatgacggc ttgtttcttt tctgtggctg cgtgaaagcc ttgaggggct  1020
ccgggagggc cctttgtgcg ggggggagcg gctcgggggg tgcgtgcgtg tgtgtgtgcg  1080
tggggagcgc cgcgtgcggc ccgcgctgcc cggcggctgt gagcgctgcg ggcgcggcgc  1140
ggggctttgt gcgctccgca gtgtgcgcga ggggagcgcg gccggggcg gtgcccgcg  1200
gtgcgggggg ggctgcgagg ggaacaaagg ctgcgtgcgg ggtgtgtgcg tgggggggtg  1260
agcaggggggt gtgggcgcgg cggtcgggct gtaaccccc cctgcacccc cctccccgag  1320
ttgctgagca cggcccggct tcgggtgcgg ggctccgtac ggggcgtggc gcggggctcg  1380
ccgtgccggg cggggggtgg cggcaggtgg gggtgccggg cggggcgggg ccgctcggg  1440
ccggggaggg ctcggggag gggcgcggcg gccccggag cgccggcggc tgtcgaggcg  1500
cggcgagccg cagccattgc cttttatggt aatcgtgcga gagggcgcag ggacttcctt  1560
tgtcccaaat ctgtgcggag ccgaaatctg ggaggcgccg ccgcacccc tctagcgggc  1620
gcggggcgaa gcggtgcggc gccggcagga aggaaatggg cggggagggc cttcgtgcgt  1680
cgccgcgccg ccgtcccctt ctccctctcc agcctcgggg ctgtccgcgg gggacggct  1740
gccttcgggg gggacgggc agggcggggt tcggcttctg gcgtgtgacc ggcggctcta  1800
gagcctctgc taaccatgtt catgccttct tcttttttcct acagctcctg gcaacgtgc  1860
tggttattgt gctgtctcat catttggca aagaattcct cgaagatcta ggcctgcagg  1920
accggactca gatctcgagg ccgccaccat gactggagca agagcatcag cagcagagca  1980
gagaagagca gggagatcag gacaggcacg ggcagcagaa agagcagcag gaatgagcgg  2040
agcaggaagg gcactggcag ctctgctgct ggcagccagt gtgctgtcag ctgcactgct  2100
ggcacctgga ggaagctccg gacgagacgc acaggcagct ccccctagag acctggataa  2160
gaaaaggcac gccgaactga agatggatca ggctctgctg ctgatccata acgagctgct  2220
gtggacaaat ctgactgtgt actggaaaag cgaatgctgt tatcactgcc tgttccaggt  2280
gctggtcaac gtgccacagt ctcccaaggc cgggaaacca agtgcagccg ctgcatctgt  2340
gagtacccag catggaagca tcctgcagct gaacgacaca cggtaggaaa aggaggtgtg  2400
caggctggaa taccgcttcg gagagtttgg caattatagc ctgctggtca aaaacattca  2460
caatggggtg tccgaaatcg cttgtgatct ggcagtcaac gaggacccag tggatagcaa  2520
tctgcccgtg tccattgcct ttctgatcgg cctggctgtc atcattgtga tttcattcct  2580
gcggctgctg ctgagcctgg acgattttaa caattggatt agcaaggcta tctctagtcg  2640
agaaacagac cggctgatca atagcgagct gggctcaccc agccggactg atcctctgga  2700
cggggatgtg cagccagcaa cctggagact gagtgcactg ccaccacgac tgagatcagt  2760
ggacactttc agaggcattg ccctgatcct gatggtcttt tgaactacg gaggcggaaa  2820
gtactggtat ttcaaacatg cttcctggaa tggactgacc gtcgcagatc tggtgttccn  2880
ctggttcgtg tttattatgg gctcaagcat ctttctgagc atgacatcca ttctgcagcn  2940
cggctgttct aagttccgac tgctgggaa aatcgcctgg aggagttttc tgctgatttg  3000
catcggaatc attatcgtga acctaatta ttgtctgggc ccactgtctt gggacaaagt  3060
caggatccca ggagtgctgc agcgactggg agtcacttac ttcgtggtcg cagtgctgga  3120
gctgctgttt gccaaacctg tgccagaaca ctgcgcctct gagcggagtt gtcgtcact  3180
gagagatatt acctcctctt ggccccagtg gctgctgatc ctggtgctgg aggggctgtg  3240
gctgggactg acattcctgc tgccagtgcc tggatgccca actgggtatc tgggacctgg  3300
aggcattggc gactttggga agtatcctaa ctgtaccggg ggaccgctg gatacatcga  3360
tcgcctgctg ctgggcacga atcacctgta ccagcatca agttcagccg tcctgtacca  3420
tacagaagtg gcttatgacc ccgagggaat tctgggcact attaatagca tcgtcatggc  3480
tttcctgggc gtgcaggcag ggaagatcct gctgtactat aaggctcgaa ctaaagatat  3540
tctgatccgc tttaccgcat ggtgctgtat tctgggcctc atcccgtcg ccctgacaaa  3600
ggtgtctgag aacgaagggt tcattcctgt caacaaaaat ctggtggtccc tgtcttatgt  3660
gaccacactg agctccttg ccttcttat cctgctggtc ctgtacccag tggtcgacgt  3720
gaagggactg tggactggca cccccttct ttacccaggg atgaactcca tcctggtcta  3780
tgtgggacac gaggtgttcg aaaattactt ccctttcag tggaagctga agataacca  3840
gtctcacaaa gagcatctga cccagaatat cgtggccaca gccctgtggg tcctgattgc  3900
ctatatcctg tatcggaaga gattttctg gaagatttga gggcgcgcc gcgactctag  3960
atcataatca gccataccac atttgtgagg ttttacttg cttaaaaaa cctcccacac  4020
ctccccctga acctgaaaca taaatgaat gcaattgttg ttgttaactt gtttattgca  4080
gcttataatg gttacaaata aagcaatga atcacaaatt tcacaaataa agcatttttt  4140
tcactgcatt ctagttgtgg gcatgctggg gagagatcta ggaacccta gtgatgagt  4200
tggcactcc ctctctgcgc gctcgctcgc tcactgaggc cgcccgggca aagcccgggc  4260
gtcgggcgac ctttggtcgc ccggcctcag tgagcgagc agcgcgcaga gagggagtgg  4320
ccaacccca ccccccccc ccctgcagcc cgcattaatg aatcggccaa cgcgcgggga  4380
gaggcggttt gcgtattggg cgctcttccg cttcctcgct cactgactcg ctgcgctcgg  4440
tcgttcggct gcggcgagcg gtatcagctc actcaaaggc ggtaatacgg ttatccacag  4500
aatcagggga taacgcagga aagaacatgt gagcaaaagg ccagcaaaag gccaggaacc  4560
gtaaaaaggc cgcgttgctg cgttttttcc ataggctccg ccccctgac gagcatcaca  4620
aaaatcgacg ctcaagtcag aggtggcgaa acccgacagg actataaaga taccaggcgt  4680
```

| | | | | | |
|---|---|---|---|---|---|
| ttcccctgg | aagctccctc | gtgcgctctc | ctgttccgac | cctgccgctt | accggatacc | 4740 |
| tgtccgcctt | tctcccttcg | ggaagcgtgg | cgctttctca | atgctcacgc | tgtaggtatc | 4800 |
| tcagttcggt | gtaggtcgtt | cgctccaagc | tgggctgtgt | gcacgaaccc | cccgttcagc | 4860 |
| ccgaccgctg | cgccttatcc | ggtaactatc | gtcttgagtc | caacccgta | agacacgact | 4920 |
| tatcgccact | ggcagcagcc | actggtaaca | ggattagcag | agcgaggtat | gtaggcggtg | 4980 |
| ctacagagtt | cttgaagtgg | tggcctaact | acggctacac | tagaaggaca | gtatttggta | 5040 |
| tctgcgctct | gctgaagcca | gttaccttcg | gaaaaagagt | tggtagctct | tgatccggca | 5100 |
| aacaaaccac | cgctggtagc | ggtggttttt | ttgtttgcaa | gcagcagatt | acgcgcagaa | 5160 |
| aaaaaggatc | tcaagaagat | cctttgatct | tttctacggg | gtctgacgct | cagtggaacg | 5220 |
| aaaactcacg | ttaagggatt | ttggtcatga | gattatcaaa | aaggatcttc | acctagatcc | 5280 |
| ttttaaatta | aaaatgaagt | tttaaatcaa | tctaaagtat | atatgagtaa | acttggtctg | 5340 |
| acagttacca | atgcttaatc | agtgaggcac | ctatctcagc | gatctgtcta | tttcgttcat | 5400 |
| ccatagttgc | ctgactcccc | gtcgtgtaga | taactacgat | acgggagggc | ttaccatctg | 5460 |
| gccccagtgc | tgcaatgata | ccgcgagacc | cacgctcacc | ggctccagat | ttatcagcaa | 5520 |
| taaaccagcc | agccggaagg | gccgagcgca | gaagtggtcc | tgcaacttta | tccgcctcca | 5580 |
| tccagtctat | taattgttgc | cgggaagcta | gagtaagtag | ttcgccagtt | aatagtttgc | 5640 |
| gcaacgttgt | tgccattgct | acaggcatcg | tggtgtcacg | ctcgtcgttt | ggtatggctt | 5700 |
| cattcagctc | cggttcccaa | cgatcaaggc | gagttacatg | atcccccatg | ttgtgcaaaa | 5760 |
| aagcggttag | ctccttcggt | cctccgatcg | ttgtcagaag | taagttggcc | gcagtgttat | 5820 |
| cactcatggt | tatgcagca | ctgcataatt | ctcttactgt | catgccatcc | gtaagatgct | 5880 |
| tttctgtgac | tggtgagtac | tcaaccaagt | cattctgaga | atagtgtatg | cggcgaccga | 5940 |
| gttgctcttg | cccggcgtca | atacgggata | ataccgcgcc | acatagcaga | actttaaaag | 6000 |
| tgctcatcat | tggaaaacgt | tcttcgggc | gaaaactctc | aaggatctta | ccgctgttga | 6060 |
| gatccagttc | gatgtaaccc | actcgtgcac | ccaactgatc | ttcagcatct | tttactttca | 6120 |
| ccagcgtttc | tgggtgagca | aaaacaggaa | ggcaaaatgc | cgcaaaaaag | ggaataaggg | 6180 |
| cgacacggaa | atgttgaata | ctcatactct | tcctttttca | atattattga | agcatttatc | 6240 |
| agggttattg | tctcatgagc | ggatacatat | ttgaatgtat | ttagaaaaat | aaacaaatag | 6300 |
| gggttccgcg | cacatttccc | cgaaaagtgc | cacctgacgt | ctaagaaacc | attattatca | 6360 |
| tgacattaac | ctataaaaat | aggcgtatca | cgaggccctt | tcgtctcgcg | cgtttcggtg | 6420 |
| atgacggtga | aaacctctga | cacatgcagc | tcccggagac | ggtcacagct | tgtctgtaag | 6480 |
| cggatgccgg | gagcagacaa | gcccgtcagg | gcgcgtcagc | gggtgttggc | gggtgtcggg | 6540 |
| gctggcttaa | ctatgcggca | tcagagcaga | ttgtactgag | agtgcaccat | atgcggtgtg | 6600 |
| aaataccgca | cagatgcgta | aggagaaaat | accgcatcag | gaaattgtaa | acgttaatat | 6660 |
| tttgttaaaa | ttcgcgttaa | attttttgtta | aatcagctca | ttttttaacc | aataggccga | 6720 |
| aatcggcaaa | atcccttata | aatcaaaaga | atagaccgag | atagggttga | gtgttgttcc | 6780 |
| agtttggaac | aagagtccac | tattaaagaa | cgtggactcc | aacgtcaaag | ggcgaaaaac | 6840 |
| cgtctatcag | ggcgatggcc | cactacgtga | accatcaccc | taatcaagtt | tttggggtc | 6900 |
| gaggtgccgt | aaagcactaa | atcggaaccc | taaaggagc | cccgatttta | gagcttgacg | 6960 |
| gggaaagccg | gcgaacgtgg | cgagaaagga | agggaagaaa | gcgaaaggag | cgggcgctag | 7020 |
| ggcgctggca | agtgtagcgg | tcacgctgcg | cgtaaccacc | acaccgccg | cgcttaatgc | 7080 |
| gccgctacag | ggcgcgtcgc | gccattcgcc | attcaggcta | cgcaactgtt | gggaagggcg | 7140 |
| atcggtgcgg | gcctcttcgc | tattacgcca | ggctgca | | | 7177 |

SEQ ID No. 2
```
MAADGYLPDW LEDTLSEGIR QWWKLKPGPP PPKPAERHKD DSRGLVLPGY KYLGPFNGLD     60
KGEPVNEADA AALEHDKAYD RQLDSGDNPY LKYNHADAEF QERLKEDTSF GGNLGRAVFQ    120
AKKRILEPLG LVEEPVKTAP GKKRPVEHSP AEPDSSSGTG KSGQQPARKR LNFGQTGDAD    180
SVPDPQPLGQ PPAAPSGLGT NTMASGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LSFKLFNIQV KEVTQNDGTT TIANNLTSTV QVFTDSEYQL PYVLGSAHQG    360
CLPPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTMSRL QFSQAGASDI RDQSRNWLPG    480
PCYRQQRVSK TAADNNNSDY SWTGATKYHL NGRDSLVNPG PAMASHKDDE EKYFPQSGVL    540
IFGKQDSGKT NVDIEKVMIT DEEEIRTTNP VATEQYGSVS TNLQSGNTQA ATSDVNTQGV    600
LPGMVWQDRD VYLQGPIWAK IPHTDGHFHP SPLMGGFGLK HPPPQILIKN TPVPANPSTT    660
FSAAKFASFI TQYSTGQVSV EIEWELQKEN SKRWNPEIQY TSNYNKSVNV DFTVDTNGVY    720
SEPRPIGTRY LTRNL                                                    735
```

SEQ ID No. 3
```
MAADGYLPDW LEDTLSEGIR QWWKLKPGPP PPKPAERHKD DSRGLVLPGY KYLGPFNGLD     60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNRQA ATADVNTQGV    600
LPGMVWQDRD VYLQGPIWAK IPHTDGHFHP SPLMGGFGLK HPPPQILIKN TPVPANPSTT    660
FSAAKFASFI TQYSTGQVSV EIEWELQKEN SKRWNPEIQY TSNYNKSVNV DFTVDTNGVY    720
SEPRPIGTRY LTRNL                                                    735
```

SEQ ID No. 4
```
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
```

```
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PPFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID No. 5
MAADGYLPDW LEDNLSEGIR EWWDLKPGAP KPKANQQKQD DGRGLVLPGY KYLGPFNGLD     60
KGEPVNAADA AALEHDKAYD QQLKAGDNPY LRYNHADAEF QERLQEDTSF GGNLGRAVFQ    120
AKKRVLEPLG LVEEGAKTAP GKKRPVEPSP QRSPDSSTGI GKKGQQPAKK RLNFGQTGDS    180
ESVPDPQPIG EPPAGPSGLG SGTMAAGGGA PMADNNEGAD GVGSSSGNWH CDSTWLGDRV    240
ITTSTRTWAL PTYNNHLYKQ ISNGTSGGST NDNTYFGYST PWGYFDFNRF HCHFSPRDWQ    300
RLINNNWGFR PKRLNFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFEFSYQFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHK DDEERFFPSS    540
GVLMFGKQGA GKDNVDYSSV MLTSEEEIKT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFSQAKLA SFITQYSTGQ VSVEIEWELQ KENSKRWNPE IQYTSNYYKS TNVDFAVNTD    720
GTYSEPRPIG TRYLTRNL                                                 738

SEQ ID No. 6
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTTTGQNNN SNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                 738
```

The invention claimed is:

1. A composition comprising an optimised heparin-α-glucosaminide N-acetyltransferase (HGSNAT) nucleic acid sequence of comprising the sequence SEQ ID No. 1 or a sequence having at least 77% homology thereof, wherein the sequence is optimised for enhanced expression or activity.

2. The composition of claim 1, wherein the sequence is a sequence having at least 95%, 98% or 99% homology thereof.

3. The composition of claim 1, wherein the optimised HGSNAT nucleic acid sequence:
   (i) has been codon optimised by selecting codons most common in human cells and/or reducing one or more secondary structures and hairpins which may form in subsequent mRNA and/or inserting a Kozak sequence at the ATG start site;
   (ii) is under the control of a CAG promoter; or
   (iii) is flanked by inverted terminal repeats and contains the cis acting elements from adeno associated virus 2 (AAV2).

4. The composition of claim 1, wherein the sequence is incorporated into an adeno associated viral (AAV) vector.

5. The composition of claim 4, wherein the AAV has a AAV2 True Type or AAV8 or AAV9 or RH10 serotype.

6. The composition of claim 1, for use in the treatment of a disease or condition attributable to heparin-α-glucosaminide N-acetyltransferase (HGSNAT) deficiency, wherein the disease or condition comprises mucopolysaccharidosis (MPS) IIIC.

7. The composition of claim 6, wherein the treatment is performed intracranially.

8. The composition of claim 6, wherein the composition is co-administered with an immunosuppressant.

9. An adeno associated viral (AAV) vector comprising an optimised heparin-α-glucosaminide N-acetyltransferase (HGSNAT) nucleic acid sequence of comprising the sequence SEQ ID No. 1 or a sequence having at least 77% homology thereof, wherein the sequence is optimised for enhanced expression or activity.

10. The vector of claim 9, wherein the sequence is a sequence having at least 95% homology thereof.

11. The vector of claim 9, wherein the vector comprises a AAV9 or a AAV8 or AAV2 True Type or a RH10 serotype.

12. The vector of claim 9, wherein the optimised HGSNAT nucleic acid sequence:
   (i) is under the control of a CAG promoter;
   (ii) is flanked by inverted terminal repeats and contains the cis acting elements from adeno associated virus 2 (AAV2); or
   (iii) has been codon optimised by selecting codons most common in human cells and/or reducing one or more secondary structures and hairpins which may form in subsequent mRNA and/or inserting a Kozak sequence at the ATG start site.

13. The vector of claim 9, wherein the vector backbone comprises the pTR-UF-11 vector backbone.

14. The vector of claim 9, for use in the treatment of a disease or condition attributable to heparin-α-glucosaminide N-acetyltransferase (HGSNAT) deficiency, wherein the disease or condition comprises mucopolysaccharidosis (MPS) IIIC.

15. The vector of claim 14, wherein the treatment is performed intracranially.

* * * * *